US009823198B2

(12) United States Patent
Faifer

(10) Patent No.: US 9,823,198 B2
(45) Date of Patent: Nov. 21, 2017

(54) METHOD AND APPARATUS FOR NON-CONTACT MEASUREMENT OF INTERNAL QUANTUM EFFICIENCY IN LIGHT EMITTING DIODE STRUCTURES

(71) Applicant: KLA-Tencor Corporation, Milpitas, CA (US)

(72) Inventor: Vladimir N. Faifer, Santa Clara, CA (US)

(73) Assignee: KLA-Tencor Corporation, Milpitas, CA (US)

(*) Notice: Subject to any disclaimer, the term of this patent is extended or adjusted under 35 U.S.C. 154(b) by 355 days.

(21) Appl. No.: 14/485,468

(22) Filed: Sep. 12, 2014

(65) Prior Publication Data

US 2015/0077741 A1    Mar. 19, 2015

Related U.S. Application Data

(60) Provisional application No. 61/877,949, filed on Sep. 14, 2013, provisional application No. 61/933,284, filed on Jan. 29, 2014.

(51) Int. Cl.

| G01N 21/00 | (2006.01) |
|---|---|
| G01N 21/66 | (2006.01) |
| G01N 33/00 | (2006.01) |
| G01R 31/26 | (2014.01) |

(52) U.S. Cl.
CPC ............. G01N 21/66 (2013.01); G01N 33/00 (2013.01); G01R 31/2635 (2013.01); *G01N 2033/0095* (2013.01)

(58) Field of Classification Search
CPC ................... G01N 21/66; G01N 33/00; G01N 2033/0095; G01R 31/2635
See application file for complete search history.

(56) References Cited

U.S. PATENT DOCUMENTS

| 7,414,409 B1* | 8/2008 | Faifer ................. G01R 31/311 324/522 |
|---|---|---|
| 2003/0122561 A1 | 7/2003 | Stokes et al. |
| 2004/0061048 A1 | 4/2004 | Vasic et al. |

(Continued)

OTHER PUBLICATIONS

PCT International Search Report, PCT/US2014/055537, dated Dec. 29, 2014.

*Primary Examiner* — Michael A Lyons
*Assistant Examiner* — Maurice Smith
(74) *Attorney, Agent, or Firm* — Suiter Swantz pc llo

(57) ABSTRACT

Non-contact measurement of one or more electrical response characteristics of a LED structure includes illuminating an illumination area of a surface of a light emitting diode structure with one or more light pulses, measuring a transient of a luminescence signal from a luminescence area within the illumination area of the light emitting diode structure with a luminescence sensor, determining a first luminescence intensity at a first time of the measured transient of the luminescence signal from the light emitting diode structure, determining a second luminescence intensity at a second time different from the first time of the measured transient of the luminescence signal from the light emitting diode structure and determining an intensity of the electroluminescence component of the luminescence signal from the light emitting diode structure based on the first luminescence signal and the second luminescence signal.

30 Claims, 18 Drawing Sheets

(56) References Cited

U.S. PATENT DOCUMENTS

2007/0170933 A1* 7/2007 Ma .................... G01N 21/6489
                                                            324/754.03
2010/0153033 A1   6/2010 Schaus et al.
2010/0219327 A1   9/2010 Arbore et al.
2011/0301892 A1  12/2011 Kamieniecki

* cited by examiner

METHOD AND APPARATUS FOR NON-CONTACT MEASUREMENT OF INTERNAL QUANTUM EFFICIENCY IN LIGHT EMITTING DIODE STRUCTURES

CROSS-REFERENCE TO RELATED APPLICATIONS

The present application claims the benefit under 35 U.S.C. §119(e) of U.S. Provisional Application Ser. No. 61/877,949, filed Sep. 14, 2013; and U.S. Provisional Application Ser. No. 61/933,284, filed Jan. 29, 2014. The U.S. Provisional Application Ser. No. 61/877,949 and U.S. Provisional Application Ser. No. 61/933,284 are incorporated herein by reference in the entirety.

TECHNICAL FIELD

The present invention generally relates to non-contact measurement of various electrical response characteristics in light emitting diode structures, and, in particular, a non-contact technique for measuring internal quantum efficiency of light emitting diode structures.

BACKGROUND

As the demand for improved semiconductor device performance continues to increase, so too does the need for improved semiconductor device characterization techniques. Semiconductor wafers, such as silicon wafers, play an important role in the fabrication of device structures. Such device structures include, but are not limited to, semiconductor structures and related features associated with light emitting diodes (e.g., MOCVD grown structures). Improved monitoring of LED quality and fabrication control is critical in the development of advanced semiconductor device fabrication techniques. Internal quantum efficiency (IQE) is a common indicator for LED performance and is important for FOEL process control for the purposes of improving yield and quality of LED devices.

One characterization technique previously used to monitor electroluminescence and IQE includes a spring loaded probe contact technique. Spring loaded contact measurement techniques are described generally in U.S. Pat. No. 7,679,381, issued on Mar. 16, 2010; U.S. Patent Publication No. 2013/0043875, filed on Dec. 21, 2011; and U.S. Patent Publication No. 2013/0046496, filed on Dec. 21, 2011, which are each incorporated herein by reference in the entirety. The spring loaded contact technique is based on the measurement of electroluminescence intensity stimulated by a forward voltage, which is applied to a spring loaded probe, with reference to a bottom n-layer. The connection to the bottom n-layer is established through edge of the wafer with a second probe.

This technique also suffers from a number of disadvantages. One of the primary disadvantages of this technique is that the electroluminescence proximate to the contact area of the probe is obstructed by the probe itself and, therefore, only peripheral and scattered portions of the luminescence signal are collected. In addition, another disadvantage of this technique includes the failure to account for the lateral current in the p-n junction layers, which may lead to significant spreading of electroluminescence outside of the electrode area, resulting in a significant contribution measurement error. Further, this method suffers from the presence of measurement artifacts related to the contamination, high contact resistance, alignment difficulties, the present of particles and the like.

It is evident that the prior art includes a number of deficiencies. Therefore, it would be desirable to provide a method and system that cure these deficiencies of the prior art identified above.

SUMMARY

An apparatus for contactless measurement of one or more characteristics of a LED structure is disclosed, in accordance with one embodiment of the present disclosure. In one illustrative embodiment, the apparatus includes an illumination unit including an illumination source for illuminating an illumination area of a substrate including a light emitting diode structure with light of a selected intensity amplitude, the light including at least one of intensity modulated light or pulsed light, the light suitable for stimulating photoluminescence within at least a first area of the light emitting diode structure of the illumination area. In one illustrative embodiment, the apparatus includes a luminescence measurement unit including at least one optical sensor configured to measure a luminescence signal from the first area of the LED structure within the illumination area. In one illustrative embodiment, the apparatus includes a junction photovoltage measurement unit including at least a first transparent electrode positioned proximate to the light emitting diode structure and configured to transmit light from the illumination source to the first area of the LED structure, wherein the first transparent electrode is configured to measure a junction photovoltage signal of the light emitting diode structure corresponding with the first area within the illuminated area, wherein the area of the first electrode is smaller than the illumination area illuminated by the illumination unit.

In one illustrative embodiment, the apparatus includes a controller communicatively coupled to at least the luminescence measurement unit, the junction photovoltage measurement unit and the illumination unit. In one illustrative embodiment, the controller may control one or more characteristics of the light from the illumination source. In one illustrative embodiment, the controller may receive one or more measurements of the luminescence signal from the luminescence measurement unit. In one illustrative embodiment, the controller may receive one or more measurements of the junction photovoltage signal from the junction photovoltage measurement unit. In one illustrative embodiment, the controller may determine at least one of an internal quantum efficiency or an internal injection efficiency of the light emitting diode structure based on one or more characteristics of the received one or more measurements of the luminescence signal and one or more characteristics of the received one or more measurements of the junction photovoltage signal.

An apparatus for contactless measurement of one or more characteristics of a LED structure is disclosed, in accordance with one embodiment of the present disclosure. In one illustrative embodiment, the apparatus includes an illumination unit including an illumination source for illuminating an illumination area of a substrate including a light emitting diode structure with light of a selected intensity amplitude, the light including at least one of intensity modulated light or pulsed light, the light suitable for stimulating photoluminescence within at least a first area of the light emitting diode structure of the illumination area. In one illustrative embodiment, the apparatus includes a luminescence measurement unit including at least one optical sensor configured to measure an electroluminescence intensity from an area of the light emitting diode structure unexposed to the intensity modulated light. In one illustrative embodiment, the apparatus includes a first junction photovoltage measurement unit including at least a first transparent electrode positioned proximate to the light emitting diode structure and configured to measure an unexposed junction photovoltage signal from the unexposed area of the light emitting diode structure. In one illustrative embodiment, the apparatus includes a second junction photovoltage measurement unit including at least a second transparent electrode positioned proximate to the light emitting diode structure, the second transparent electrode encompassing the first transparent electrode and configured to measure an exposed junction photovoltage signal from the illumination area of the light emitting diode structure external to the first transparent electrode.

In one illustrative embodiment, the apparatus includes a controller communicatively coupled to at least the luminescence measurement unit, the first junction photovoltage measurement unit, the second junction photovoltage measurement unit and the illumination unit. In one illustrative embodiment, the controller may control one or more characteristics of the light from the illumination source. In one illustrative embodiment, the controller may receive one or more measurements of the electroluminescence signal from the luminescence measurement unit. In one illustrative embodiment, the controller may receive one or more measurements of the unexposed junction photovoltage signal from the first junction photovoltage measurement unit. In one illustrative embodiment, the controller may receive one or more measurements of the exposed junction photovoltage signal from the second junction photovoltage measurement unit. In one illustrative embodiment, the controller may determine a photocurrent density of the light emitting diode structure with the measured unexposed junction photovoltage and the measured exposed junction photovoltage. In one illustrative embodiment, the controller may determine a forward voltage of the light emitting diode structure based on one or more additional junction photovoltage measurements from the first transparent electrode and one or more additional junction photovoltage measurements from the second transparent electrode. In one illustrative embodiment, the controller may determine an internal quantum efficiency of the light emitting diode structure with at least one of the measured electroluminescence intensity from the unexposed area of the light emitting diode structure, the determined photocurrent density of the light emitting diode structure or the determined forward voltage of the light emitting diode structure.

An apparatus for contactless measurement of one or more characteristics of a LED structure is disclosed, in accordance with one embodiment of the present disclosure. In one illustrative embodiment, the apparatus includes an illumination unit including an illumination source for illuminating an illumination area of a substrate including a light emitting diode structure with light of a selected intensity amplitude, the light including at least one of intensity modulated light or pulsed light, the light suitable for stimulating photoluminescence within at least a first area of the light emitting diode structure of the illumination area. In one illustrative embodiment, the apparatus includes a luminescence measurement unit including at least one optical sensor configured to measure an electroluminescence intensity from an area of the light emitting diode structure unexposed to the intensity modulated light. In one illustrative embodiment, the apparatus includes a first junction photovoltage measurement unit including at least a first transparent electrode positioned proximate to the light emitting diode structure and configured to measure an exposed junction photovoltage signal from the exposed area of the light emitting diode structure. In one illustrative embodiment, the apparatus includes a second junction photovoltage measurement unit including at least a second transparent electrode positioned proximate to the light emitting diode structure, the second transparent electrode encompassing the first transparent electrode and configured to measure an unexposed junction photovoltage signal from the illumination area of the light emitting diode structure external to the first transparent electrode. In one illustrative embodiment, the apparatus includes a controller communicatively coupled to at least the luminescence measurement unit, the first junction photovoltage measurement unit, the second junction photovoltage measurement unit and the illumination unit. In one illustrative embodiment, the controller may control one or more characteristics of the light from the illumination source. In one illustrative embodiment, the controller may receive one or more measurements of the electroluminescence signal from the luminescence measurement unit. In one illustrative embodiment, the controller may receive one or more measurements of the exposed junction photovoltage signal from the first junction photovoltage measurement unit. In one illustrative embodiment, the controller may receive one or more measurements of the unexposed junction photovoltage signal from the second junction photovoltage measurement unit. In one illustrative embodiment, the controller may determine a photocurrent density of the light emitting diode structure with the measured unexposed junction photovoltage and the measured exposed junction photovoltage. In one illustrative embodiment, the controller may determine a forward voltage of the light emitting diode structure based on one or more additional junction photovoltage measurements from the first transparent electrode and one or more additional junction photovoltage measurements from the second transparent electrode. In one illustrative embodiment, the controller may determine an internal quantum efficiency of the light emitting diode structure with at least one of the measured electroluminescence intensity from the unexposed area of the light emitting diode structure, the determined photocurrent density of the light emitting diode structure or the determined forward voltage of the light emitting diode structure.

A method for contactless measurement of one or more characteristics of a LED structure is disclosed, in accordance with one embodiment of the present disclosure. In one illustrative embodiment, the method includes illuminating an illumination area of a surface of a light emitting diode structure with one or more light pulses. In one illustrative embodiment, the method includes measuring a transient of a luminescence signal from a luminescence area within the illumination area with a luminescence sensor. In one illustrative embodiment, the method includes measuring a transient of a junction photovoltage signal from the luminescence area within the illumination area with a transparent electrode positioned within the illumination area and proximate to the surface of the light emitting diode structure. In one illustrative embodiment, the method includes determining a junction photovoltage forward voltage of the light emitting diode structure from the luminescence area. In one illustrative embodiment, the method includes determining a photocurrent density of the light emitting diode structure. In one illustrative embodiment, the method includes determining an intensity of an electroluminescence component of the luminescence signal. In one illustrative embodiment, the method includes determining at least one of an internal quantum efficiency or an internal injection efficiency of the light emitting diode structure with at least one of the determined junction photovoltage forward voltage of the light emitting diode structure from the luminescence area, the photocurrent density of the light emitting diode structure or the intensity of the electroluminescence component of the luminescence signal.

A method for contactless measurement of one or more characteristics of a LED structure is disclosed, in accordance with one embodiment of the present disclosure. In one illustrative embodiment, the method includes illuminating an illumination area of a surface of a light emitting diode structure with one or more light pulses. In one illustrative embodiment, the method includes measuring a transient of a luminescence signal from a luminescence area within the illumination area of the light emitting diode structure with a luminescence sensor. In one illustrative embodiment, the method includes determining a first luminescence intensity at a first time of the measured transient of the luminescence signal from the light emitting diode structure. In one illustrative embodiment, the method includes determining a second luminescence intensity at a second time different from the first time of the measured transient of the luminescence signal from the light emitting diode structure. In one illustrative embodiment, the method includes determining an intensity of the electroluminescence component of the luminescence signal from the light emitting diode structure based on the first luminescence signal and the second luminescence signal.

A method for contactless measurement of one or more characteristics of a LED structure is disclosed, in accordance with one embodiment of the present disclosure. In one illustrative embodiment, the method includes illuminating an illumination area of a surface of a light emitting diode structure with one or more first light pulses of a first pulse duration. In one illustrative embodiment, the method includes illuminating the illumination area of the surface of the light emitting diode structure with one or more second light pulses of a second pulse duration. In one illustrative embodiment, the method includes measuring a first luminescence intensity from the light emitting diode structure stimulated by the one or more first light pulses. In one illustrative embodiment, the method includes measuring a second luminescence intensity from the light emitting diode structure stimulated by the one or more second light pulses. In one illustrative embodiment, the method includes determining an intensity of the electroluminescence component of the luminescence signal from the light emitting diode structure based on the first luminescence intensity and the second luminescence intensity.

A method for contactless measurement of one or more characteristics of a LED structure is disclosed, in accordance with one embodiment of the present disclosure. In one illustrative embodiment, the method includes illuminating an illumination area of a surface of a light emitting diode structure with intensity modulated light. In one illustrative embodiment, the method includes measuring an electroluminescence intensity induced by photocarrier drift from an area of the light emitting diode unexposed to the intensity modulated light with a luminescence sensor. In one illustrative embodiment, the method includes measuring an unexposed junction photovoltage signal from the unexposed area of the light emitting diode structure with a first transparent electrode positioned within the unexposed area and proximate to the surface of the light emitting diode structure. In one illustrative embodiment, the method includes measuring an exposed junction photovoltage signal from the illumination area of the light emitting diode structure with a second transparent electrode external to the first transparent electrode, positioned within the illumination area and proximate to the surface of the light emitting diode structure. In one illustrative embodiment, the method includes determining a photocurrent density of the light emitting diode structure with the measured unexposed junction photovoltage and the measured exposed junction photovoltage. In one illustrative embodiment, the method includes measuring a forward voltage of the light emitting diode structure. In one illustrative embodiment, the method includes determining an internal quantum efficiency of the light emitting diode structure with at least one of the measured electroluminescence intensity from the unexposed area of the light emitting diode structure, the determined photocurrent density of the light emitting diode structure or the measured forward voltage of the diode structure.

A method for contactless measurement of one or more characteristics of a LED structure is disclosed, in accordance with one embodiment of the present disclosure. In one illustrative embodiment, the method includes illuminating an illumination area of a surface of a light emitting diode structure with intensity modulated light. In one illustrative embodiment, the method includes measuring an electroluminescence intensity induced by photocarrier drift from an area of the light emitting diode unexposed to the intensity modulated light with a luminescence sensor. In one illustrative embodiment, the method includes measuring an exposed junction photovoltage signal from the exposed area of the light emitting diode structure with a first transparent electrode positioned within the exposed area and proximate to the surface of the light emitting diode structure. In one illustrative embodiment, the method includes measuring an unexposed junction photovoltage signal from the illumination area of the light emitting diode structure with a second transparent electrode encompassing the first transparent electrode and proximate to the surface of the light emitting diode structure. In one illustrative embodiment, the method includes determining a photocurrent density of the light emitting diode structure with the measured unexposed junction photovoltage and the measured exposed junction photovoltage. In one illustrative embodiment, the method includes measuring a forward voltage of the light emitting diode structure. In one illustrative embodiment, the method includes determining an internal quantum efficiency of the light emitting diode structure with at least one of the measured electroluminescence intensity from the unexposed area of the light emitting diode structure, the determined photocurrent density of the light emitting diode structure or the measured forward voltage of the diode structure.

A method for contactless measurement of one or more characteristics of a LED structure is disclosed, in accordance with one embodiment of the present disclosure. In one illustrative embodiment, the method includes illuminating an illumination area of a surface of a light emitting diode structure with intensity modulated light. In one illustrative embodiment, the method includes measuring an intensity of the intensity modulated light. In one illustrative embodiment, the method includes measuring an electroluminescence intensity induced by photocarrier drift from an area of the light emitting diode structure unexposed to the intensity modulated light with a luminescence sensor. In one illustrative embodiment, the method includes determining an electroluminescence efficiency by comparing the electroluminescence intensity to the intensity of the modulated light.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

Figure 1A:
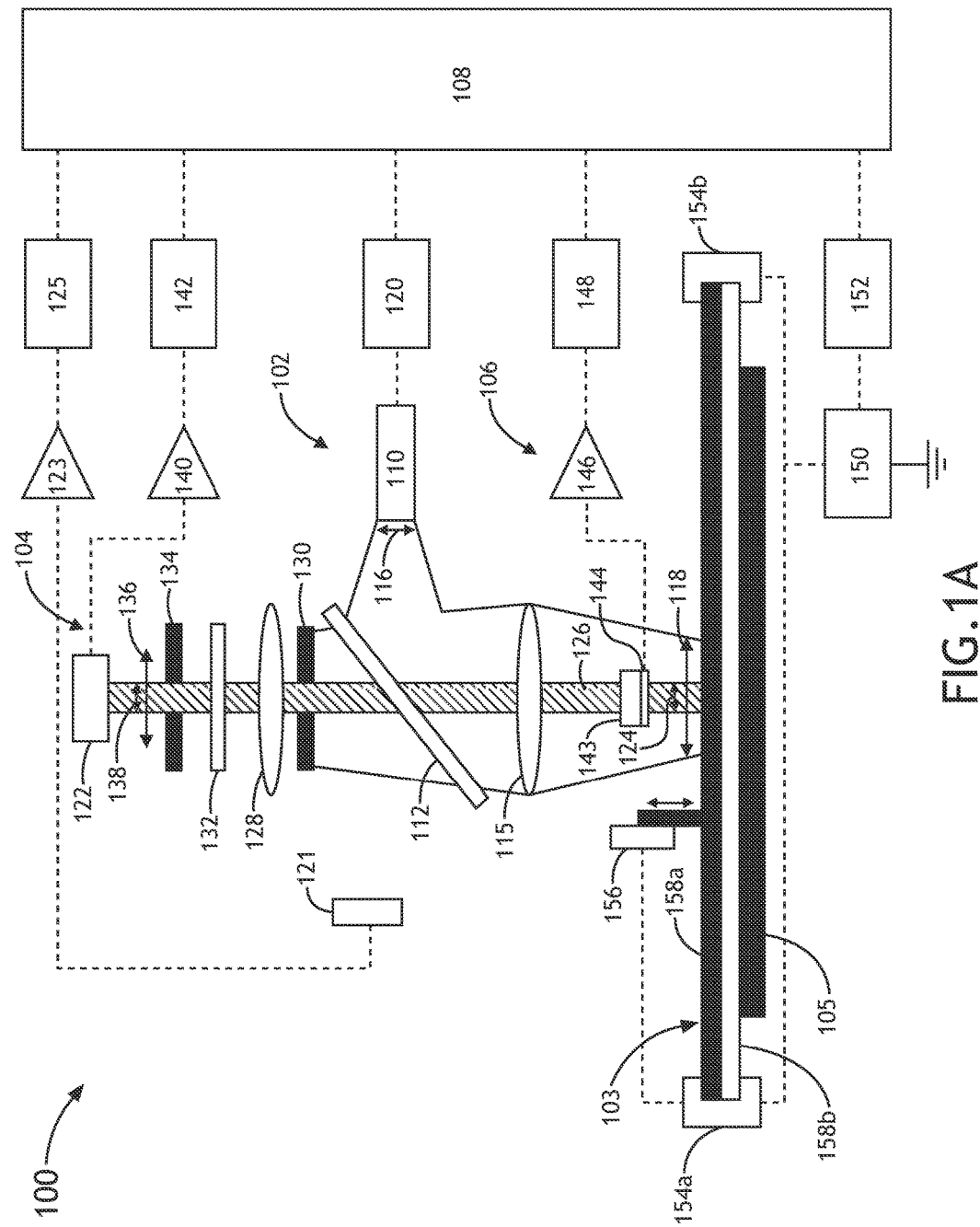
FIG. 1A is a block diagram illustrating an apparatus for contactless measurement of one or more characteristics of a LED structure, in accordance with one embodiment of the present disclosure.

It is evident that the prior art includes a number of deficiencies. Therefore, it would be desirable to provide a method and system that cure these deficiencies of the prior art identified above.

DETAILED DESCRIPTION OF THE INVENTION

Reference will now be made in detail to the subject matter disclosed, which is illustrated in the accompanying drawings.

Referring generally to FIGS. 1A through 4C, a system and method for contactless measurement of one or more characteristics of a light emitting diode (LED) structure is described in accordance with the present disclosure. Embodiments of the present inventions are directed to a luminescent measurement technique suitable for measuring electroluminescence (EL) response and/or photoluminescence (PL) response from an LED structure illuminated with excitation illumination. In addition, embodiments of the present disclosure are directed to a non-contact junction photovoltage (JPV) technique suitable for measuring various electrical response characteristics of the LED structure of a semiconductor substrate, in areas illuminated by the excitation illumination and/or area not illuminated by the excitation illumination.

The non-contact measurement technique(s) described throughout the present disclosure provide for accurate measurement of one or more characteristics of a LED structure. In some embodiments, the non-contact measurement technique(s) of the present disclosure may provide, but are not limited to, the monitoring of photocurrent, forward voltage, EL, internal quantum efficiency, injection and radiative efficiencies.

By way of non-limiting example, the techniques described throughout the present disclosure may provide for the monitoring of photocurrent, forward voltage, EL, internal quantum efficiency, injection and radiative efficiencies in LED structures after metal organic chemical vapor deposition (MOCVD) growth and anneal. By way of another non-limiting example, the techniques described throughout the present disclosure may provide for the monitoring of photocurrent, forward voltage, EL, internal quantum efficiency, injection and radiative efficiencies following plasma-enhanced chemical vapor deposition (PECVD) of conductive and transparent windows.

One or more of the above characteristics may be found using measured quantities of luminescence intensity from the LED structure. In addition, one or more of the above characteristics may be found using measured quantities of a junction photovoltage from the LED structure.

Embodiments of the present disclosure provide for non-contact measurement of electroluminescence from an optically excited LED structure via time-resolved and spatial separation of JPV-stimulated direct photoluminescence and electroluminescence. This embodiment may provide for non-contact monitoring of optically stimulated electroluminescence and associated efficiencies collected in the middle of an excitation area using a time-resolved approach following MOCVD and anneal. The results of this monitoring process may then be used as feedback for process control purposes during fabrication Additional embodiments of the present disclosure may utilize optical excitation in a first region (or regions) of the LED structure, while collecting an electroluminescence signal from a second region (or regions) of the LED structure that is outside of the first region, whereby the electroluminescence signal is stimulated by the spreading of JPV signal caused by the lateral electric field and photocurrent. This embodiment may be particularly useful in monitoring LED structures after deposition or growth of conducting and transparent windows with low sheet resistance, which leads to high spreading of JPV outside of the illumination area.

Referring now to FIG. 1A, in one embodiment, the system 100 includes an illumination unit 102. In another embodiment, the system 100 includes a luminescent measurement unit 104. In another embodiment, the system 100 includes a junction photovoltage (JPV) measurement unit 106. In another embodiment, the system 100 includes a controller 108 communicatively coupled to the illumination unit 102, the luminescence measurement unit 104 and/or the JPV measurement unit 104. It is noted herein that the JPV measurement unit 106 depicted in FIG. 1A is not a requirement of the present invention. As such, while the present disclosure focuses on embodiments including the JPV measurement unit 106, this feature should not be interpreted as a limitation on the present invention.

In one embodiment, the controller 108 is configured to direct the illumination unit 102 to illuminate a semiconductor substrate including a LED structure 103 with light having one or more selected characteristics (e.g., intensity, modulation frequency and the like). In turn, the controller 108 may receive measurements of various response characteristics of the LED structure 103, such as a PL signal and EL signal from luminescence measurement unit 104 and/or a JPV signal from JPV measurement unit 106. Further, the controller 108 may determine the photocurrent density, forward voltage, the internal quantum efficiency (IQE) and/or an internal injection efficiency of one or more LED structures 103 of a semiconductor substrate based on the measured characteristics and the various relationships described throughout the present disclosure.

In one embodiment, the illumination unit 102 includes one or more illumination sources 110. In one embodiment, the one or more illumination sources 110 are arranged to illuminate an area of a semiconductor substrate including a LED structure 103 with illumination 116. For example, the illumination source 110 may be arranged to illuminate a first illumination area 118 of the substrate including an LED structure 103.

In another embodiment, the illumination source 110 illuminates the surface of the LED structure 103 with light at one or more selected intensities. In another embodiment, the illumination source 110 illuminates the surface of the LED structure 103 with light at one or more selected modulation frequencies. For example, the illumination source 110 may output a light signal modulated at a selected modulation frequency. For instance, the modulation frequency of the light may correspond to a steady-state condition (e.g., low modulation frequency) or a non-steady-state condition (e.g., high modulation frequency). By way of another example, the illumination source 110 may output a pulsed light signal.

In another embodiment, the illumination unit 102 illuminates the surface of the LED structure 103 with light including a selected wavelength or range of wavelengths.

The illumination source 110 may include any illumination source known in the art suitable for uniformly illuminating a selected area of a substrate with modulated or pulsed light. For example, the illumination source 110 may include, but not limited to, one or more LEDs, one or more lasers, a flashlamp (e.g., filtered flashlamp), or a shuttered lamp.

In another embodiment, the illumination unit 102 includes a power source and/or signal generator 120 coupled to the illumination source 110 and the controller 108. In this regard, the controller 108 may direct the signal generator 120 to drive the illumination source 110 in order to generate a desired illumination output. For example, the signal generator 120 may cause the illumination source 110 to output a modulated light signal having a selected modulation frequency. By way of another example, the signal generator 120 may cause the illumination source 110 to output one or more light pulses of a selected duration (i.e., pulsed light signal). By way of another example, the signal generator 120 may cause the illumination source 110 to output one or more light pulses of a selected intensity. For example, the signal generator 120 may cause the illumination source 110 to output a modulated light signal having a modulation frequency sufficiently low to cause a steady-state condition in the stimulated JPV signal of the LED structure 103. By way of another example, the signal generator 120 may cause the illumination source 110 to output a modulated light signal having a modulation frequency sufficiently high to cause a non-steady-state condition in the stimulated JPV signal of the LED structure 103.

In another embodiment, the JPV measurement unit 106 includes a first transparent electrode 144 for measuring a JPV signal for a selected area within the illuminated area 118 of the LED structure 103. In one embodiment, the transparent electrode 144 is positioned proximate to the LED structure 103 and configured to transmit light from the illumination source 110 to the surface of the LED structure 103. In this regard, the first transparent electrode 144 has a first area for measuring the JPV corresponding with the first area (i.e., area subtended by the first electrode 144) within the illumination area 118 of the LED structure 103. In one embodiment, the first area of the first electrode 144 is selected to be smaller than the area illuminated by the illumination source 110. It is noted herein that selecting an area of first electrode 144 smaller than the illumination area 118 aids in limiting the impact of lateral spreading of the junction photovoltage signal beyond the illumination area 118, where the electroluminescence is also reduced as a result of the JPV spreading. It is further noted herein that the first electrode 144 may take on any suitable shape known in the art. For example, the first transparent electrode 144 may take on a circular disk shape, a square shape, rectangle shape, an oval shape, a polygonal shape and the like.

In another embodiment, the first transparent electrode 144 is disposed on a surface of a transparent element 143. In this regard, the first transparent electrode 144 may be disposed on the surface of the transparent element 143 facing the LED structure 103, as shown in FIG. 1A. In one embodiment, the first transparent electrode 144 may be disposed on the bottom surface of the transparent element 143. In another embodiment, the transparent element 143 may include, but is not limited to, one or more transparent plates 143, as shown in FIG. 1A. For example, the transparent element 143 may include, but is not limited to, a glass plate. It is noted herein that the construction of the transparent element 143 is not limited to a glass plate or a single plate configuration.

Rather, the description provided above is provided merely for illustrative purposes. It is noted herein that any material transparent to the illumination emitted by the illumination source 110 (and the stimulated PL illumination 126) is suitable for implementation within the context of the present invention. Further, the transparent element 143 may include multiple transparent plates or an alternative structure or structures suitable for securing the first electrode 144 (and additional electrode 202). It is noted herein that V. Faifer et al. describe non-contact JPV measurements in U.S. patent application Ser. No. 14/475,025, filed on Sep. 2, 2014, which is incorporated herein by reference in the entirety.

In another embodiment, the illumination unit 102 may include one or more illumination optical elements. In one embodiment, the illumination unit 102 includes one or more lenses 115. In one embodiment, the lens 115 optically couples the output of the illumination source 110 with the surface of the LED structure 103. In this regard, illumination 116 from the illumination source 110 may be directed toward the substrate 103, via beam splitter 112, and pass through the lens 115, the transparent element 143 and the first transparent electrode 144 prior to impinging on the LED structure 103 surface, as shown in FIG. 1A. It is noted herein that optical configuration of system 100 is not limited to various optical components described in the present disclosure. Rather, the various optical components and their configurations are provided merely for illustrative purposes. The system 100 may include any optical element known in the art suitable to collect, focus, direct and/or filter illumination emitted by the illumination source 110. It is contemplated herein that the system 100 may include any suitable illumination source and optical element combination known in the art. For example, any number of optical elements (e.g., fly's eye, microlens array, diffuser(s), lenses, mirrors, filters, polarizers and the like) may be used with any illumination source known in the art. For instance, one or more fiber bundles may be coupled with an illumination source (e.g., flash lamp).

In another embodiment, the luminescence measurement unit 104 includes one or more signal processing elements configured to process a measured signal prior to transmission to the controller 108. For example, the luminescence measurement unit 104 may include, but is not limited to, a preamplifier 140 for amplifying the signal from the sensor 122. In another embodiment, the luminescence measurement unit 104 includes a demodulator and/or a detector 142. Further, upon amplification, demodulation and/or detection, the signal from the sensor 122 is received by an interface of the controller 108.

In another embodiment, the luminescence measurement unit 104 includes one or more sensors 122 for sensing luminescence illumination 126 (e.g., electroluminescence (EL) illumination and/or photoluminescence (PL) illumination) from the LED structure 103. In this regard, the one or more sensors 122 may be arranged to collect and measure PL light stimulated by the light from the illumination source 110 and/or EL light stimulated by optical excitation. In another embodiment, the luminescence measurement unit 104 may include one or more optical elements. In one embodiment, lenses 115 and 128 are arranged to collect and focus luminescence illumination (e.g., electroluminescence and/or photoluminescence) generated at the LED structure 103 onto the one or more sensors 122. In another embodiment, the luminescence measurement unit 104 includes one or more diaphragms 130, 134. In one embodiment, the one or more diaphragms 130, 134 are arranged to provide luminescence collection from a central region 124 of the illumination area 118 proximate to the first transparent electrode 144. In this regard, the sensor 122 may measure a luminescence signal, including the PL and/or EL components of the signal, from a region 124 within the first illumination area 118 probed by the first transparent electrode 144.

For example, the illumination 116 emitted by the illumination source 110 may be transferred into its image 118 (e.g., illumination area 118) at the surface of the substrate including a LED structure 103 via beam splitter 112 and lens 115. In this regard, the light impinging on LED structure 103 may serve to optically excite one or more regions of the illuminated area 118. In turn, a luminescence signal is emitted by the illumination area 118 of the LED structure 103. Further, the lenses 115 and 128 may transfer the image 118 into image 136 on the sensor 122. In another embodiment, the diaphragm 134 serves to transfer luminescence light from central region 124, located within image 118, into image 138, located within image 136. In this regard, the diaphragm 134 serves to exclude collection of luminescence from the outside edge of the illumination area 118, where electroluminescence can be significantly decreased due to the spreading of the JPV signal outside of illumination area 118. For instance, in the case of GaInN deposited on sapphire, luminescence light may extend to large distances outside of illumination area 118. In one embodiment, in order to decrease collection of scattered luminescence, the additional diaphragm 130 limits the collection to luminescence light 126 to that emanates substantially perpendicularly to the surface of the LED structure 103 and collected in image 138 of the sensor 122.

In another embodiment, the luminescence measurement unit 104 includes one or more filters 132. For example, filter 132 may serve to block light from the illumination source 110, while transmitting PL light 126 emanating from the LED structure 103.

The one or more sensors 122 may include any light sensor known in the art suitable for collecting and measuring one or more characteristics associated with the stimulated PL light 126. For example, the one or more sensors 122 may include, but are not limited to, a photodector or a monochromator equipped with an array of photodetectors. In another embodiment, the one or more sensors 122 may include a spectrometer. For example, the one or more sensors 122 may include, but are not limited to, a spectrometer equipped with a photodetector array.

In another embodiment, the JPV measurement unit 106 includes one or more signal processing elements configured to process a measured signal prior to transmission to the controller 108. For example, the JPV measurement unit 106 may include, but is not limited to, a preamplifier 146 for amplifying the signal from the electrode 144. In another embodiment, the JPV measurement unit 106 includes a demodulator and/or a detector 148. Further, upon amplification, demodulation and/or detection, the signal from the electrode 144 is received by an interface of the controller 108.

In another embodiment, the detectors 142 and 148 may operate in lock-in amplification mode. In another embodiment, the detectors 142 and 148 may operate in peak detection mode.

In another embodiment, the illumination unit 102 may include an additional sensor 121 for monitoring one or more characteristics (e.g., intensity, modulation frequency, wavelength and the like) of the illumination 116 emitted by the illumination source 110. For example, the additional sensor 121 may include, but is not limited to, one or more photodetectors. In another embodiment, the additional sensor 121 is communicatively coupled to one or more signal processing elements for processing the output of the additional sensor 121 upon detection of light from the illumination source 110. For example, the one or more signal processing elements may include any signal processing circuitry known in the art, such as, but not limited to, one or more amplifiers 123 and/or one or more detectors 125. In another embodiment, the output of the detector 125 is coupled to the controller 108. In this regard, the controller 108 may monitor the output of the additional sensor 121 and thus the performance of the illumination source 110.

In another embodiment, although not shown, the system 100 may include a second additional sensor for monitoring one or more characteristics (e.g., intensity, wavelength and the like) of the illumination reflected or scattered from the surface of the LED structure 103. In another embodiment, the second additional sensor may also be coupled to one or more signal processing elements (e.g., amplifier, detector and the like), which process the output of the second additional sensor and couple the output to the controller 108.

In one embodiment, the semiconductor substrate including one or more LED structures 103 (e.g., LED layers) is disposed on a chuck 105. In another embodiment, the chuck 105 includes a conducting chuck (e.g., metal chuck). In another embodiment, the chuck 105 includes a metal chuck connected to ground. In another embodiment, the system 100 includes a signal generator 152 coupled to the wafer chuck 105 through switch 150. For example, although not shown in FIG. 1A, the switch 150 may be directly coupled to the chuck 105. In another embodiment, the switch 150 is couple to ground. In another embodiment, the signal generator 152 is coupled to controller 108, whereby the controller 108 may direct the signal generator 152 to apply a selected signal to the chuck 105. In one embodiment, the signal generator 152 may apply one or more calibration signals (e.g., impulses) to aid in measuring accurate signals of the present disclosure (e.g., JPV signal). For example, the signal generator 152 may be used to apply an AC signal to the chuck 105 through switch 150 in order to calibrate one or more photovoltage signals It is noted herein that the chuck 105 is not limited to a conducting or metal chuck and the description above is provided merely for illustrative purposes. For example, the chuck 105 may include a non-conducting chuck. In one embodiment, one or more calibrating signals of the present disclosures may be applied to the edge of the semiconductor substrate 103 (rather than through the chuck 105, as described previously herein).

In one embodiment, the system 100 may include a movable spring loaded electrode 156 (e.g., metal or conducting polymer). In one embodiment, the spring loaded electrode 156 is coupled to one or more conducting pads 154a, 154b, such as, but not limited to, metal pads or conducting polymer pads. In another embodiment, the electrode 156 may provide an electrical connection between the top-layer 158a (e.g., p-layer) and the bottom-layer 158b of the LED structure via the conducting pads 154a, 154b. For example, the spring loaded electrode 156 may be positioned near the transparent electrode 144, thereby providing a conduction pathway between a region of the top-layer 158a near the transparent electrode 144 and the bottom-layer 158b. In another embodiment, the one or more conducting pads 154a, 154b may be electrically coupled to the output of switch 150. It is noted herein that V. Faifer et al. describe the calibration of JPV measurements in U.S. patent application Ser. No. 14/475,025, filed on Sep. 2, 2014, which is incorporated above in the entirety.

Figure 1B:
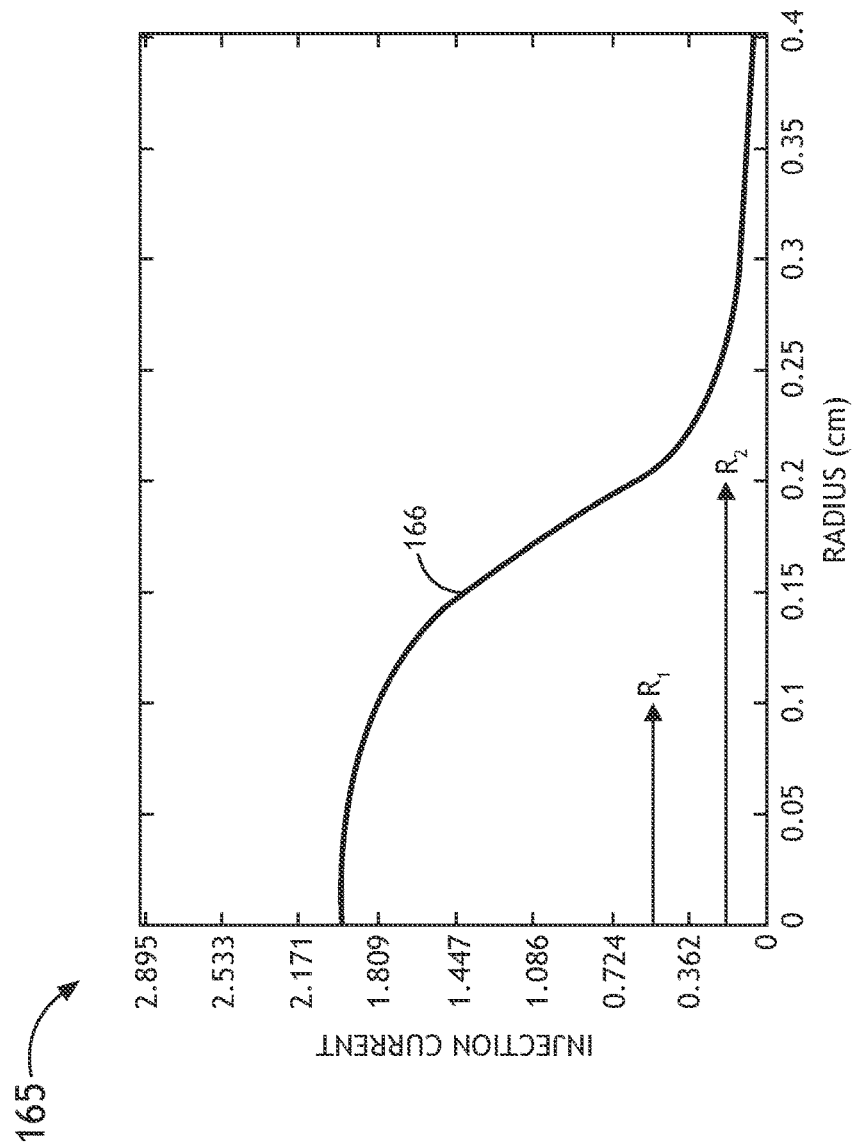
FIG. 1B illustrates a graph of injection current as a function of radius, in accordance with one embodiment of the present disclosure.

FIG. 1B illustrates a graph 165 depicting a simulated distribution 166 of junction injection current as a function of radius, in accordance with one or more embodiments of the present disclosure. It is noted herein that the simulated distribution 166 takes into account the lateral drift of carriers outside of the illumination area 118 and was calculated for a LED structure 103 with a photocurrent density of photocurrent density 20 mA/mm$^2$ and a sheet resistance of the top-layer of 20 Ohm/sq., which represent common values for semiconductor structures such as, but not limited to, GaInN structures with TCO coating or AlGaInP LED structures. It is noted herein that, in the case of the simulation represented in FIG. 1B, the electroluminescence contribution to the overall luminescence signal increases as the area of collection of the luminescence signal 126 decreases. For example, as shown in FIG. 1B, the electroluminescence contribution to the overall luminescence signal measured by sensor 121 may be higher if collected from an area defined by a radius of $r_1$=1 mm than if the collected area corresponds to a radius of $r_2$=2 mm.

Figure 1C:
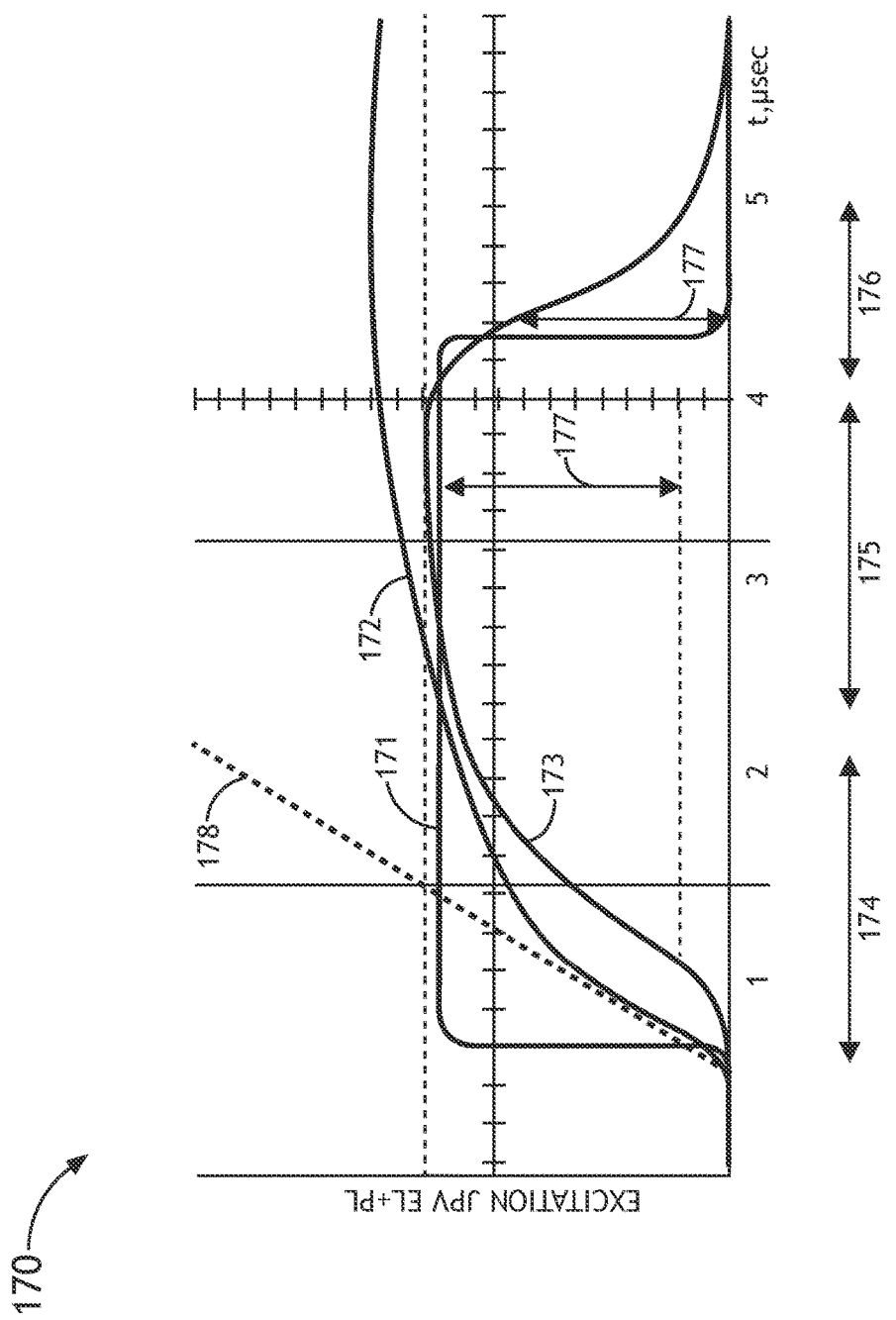
FIG. 1C illustrates a graph depicting a pulsed excitation illumination transient, a junction photovoltage transient and a luminescence transient, in accordance with one embodiment of the present disclosure.

FIG. 1C illustrates a conceptual view of an excitation illumination curve 171 and the resulting JPV transient 172 and luminescence transient 173 as a function of time, in accordance with one or more embodiments of the present invention. In this regard, the excitation illumination curve 171 and the resulting JPV transient 172 and luminescence transient 173 are plotted across various time intervals. For example, time interval 174 represents the time duration $\tau_{JPV}$ associated with the increase in the JPV signal 172 measured with transparent electrode 144 and the luminescence signal measured with sensor 122. Further, time interval 175 represents the onset of a general steady state condition in the excitation illumination curve 171 when photocurrent density is substantially equal to injection current, the JPV signal 172 and/or the luminescence signal 173. In addition, time interval 176 represents the time span associated with electroluminescence decay. In this regard, the arrows 177 represent a conceptual view of the magnitude of the electroluminescence component of the overall luminescence signal. Further, line 178 represents a conceptual view of the derivative of the JPV signal at the front side of JPV signal 172, which may be used when calculating photocurrent density $J_L$, described in additional detail further herein.

Figure 1D:
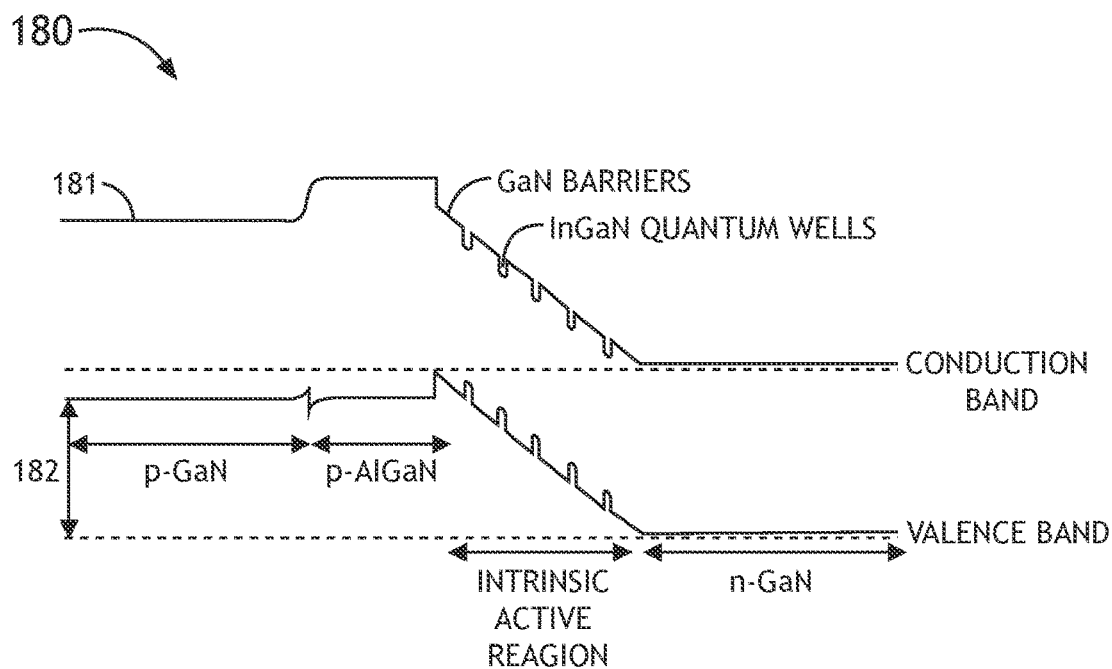
FIGS. 1D and 1E illustrate conceptual views of band diagrams of a LED structure under a dark illumination condition and an illumination condition, in accordance with one embodiment of the present disclosure.
Figure 1E:
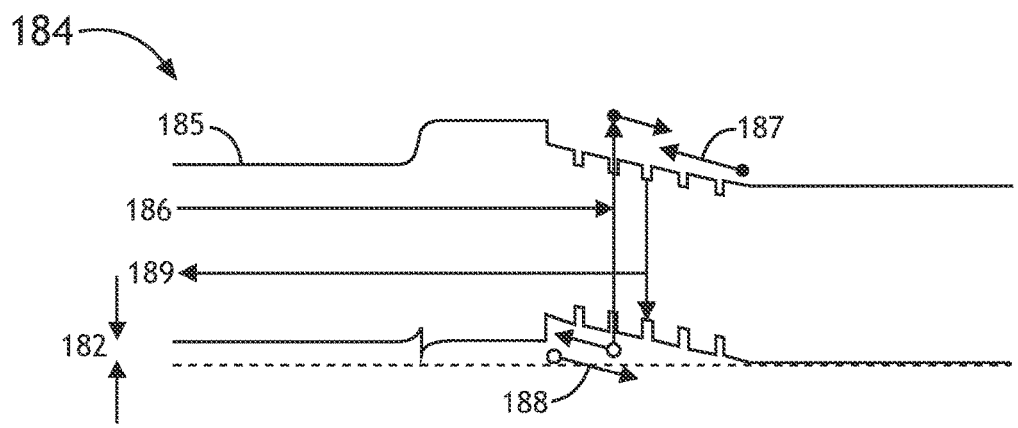

FIGS. 1D and 1E illustrate conceptual views 180, 184 of band diagrams of a LED structure 103 under a dark illumination condition 181 and an illumination condition 185. It is noted herein that the optical excitation 186 with light having a photon energy higher than the band gap leads to generation of electron-hole pairs. The excess electron-hole pairs are separated in the electric field in intrinsic active layer forming a photocurrent. Further, the build-in voltage 182 decreases and the resulting JPV signal (e.g., forward voltage as difference of build-in voltage under illumination condition and build-in voltage under dark condition) stimulates injection of electrons from n-layer 187 and holes 188 from p-layer into the active layer. It is further noted herein that their recombination in quantum wells leads to the emission of electroluminescence 189.

Figure 1F:
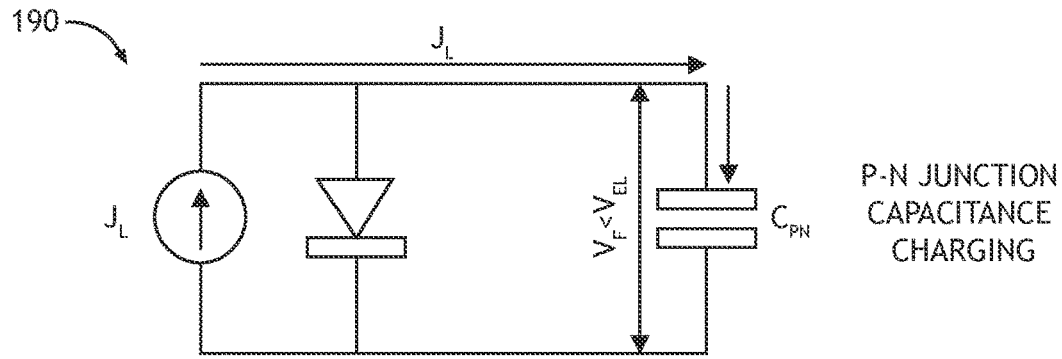
FIGS. 1F-1H illustrate a series of equivalent circuit configurations to explain the JPV time delay, the luminescence time delay and the steady state time interval, in accordance with one or more embodiments of the present disclosure.
Figure 1G:
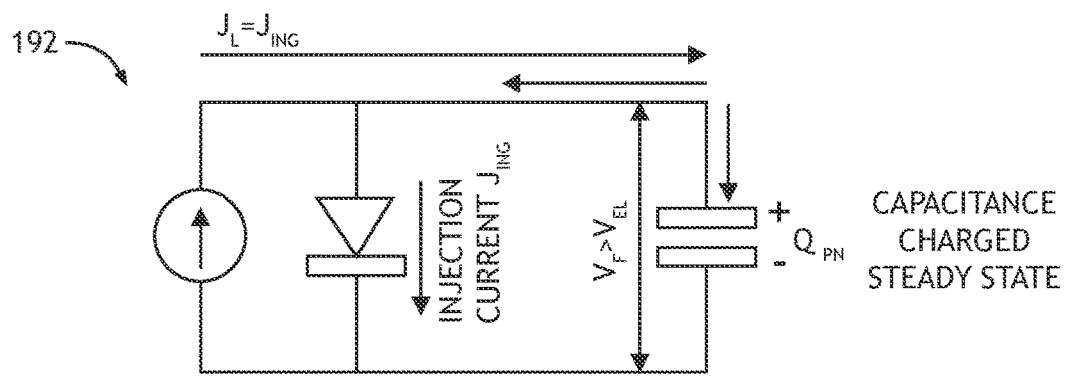
Figure 1H:
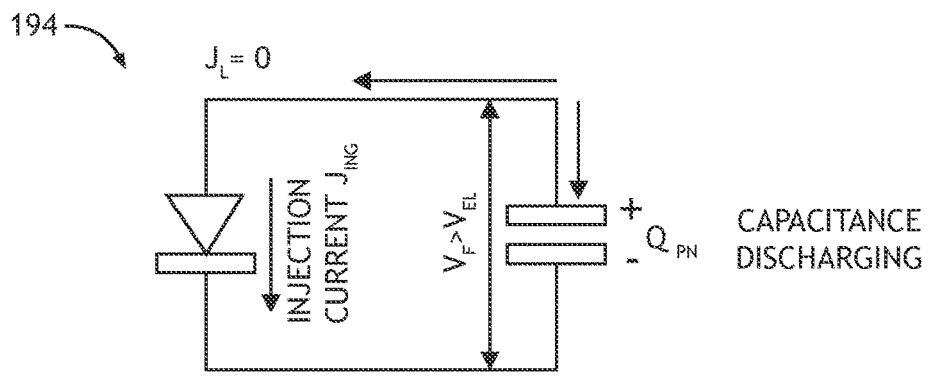

FIGS. 1F-1H illustrate a series of equivalent circuit configurations to explain the JPV time interval 174, the luminescence time interval 176 and the steady state time interval 175, discussed previously herein and depicted in FIG. 1C. As shown in equivalent circuit 190 of FIG. 1F, in time interval $0<t<\tau_{JPV}$ 174, the photocurrent, $J_L$, is acting to charge the p-n junction barrier and diffusion capacitance, Cpn. It is noted herein that in the time interval 174 the injection current, $J_{INJ}$, and forward voltage $V_F$ are low such that $V_F<V_{EL}$ (where $V_{EL}$ is electroluminescence turn-on voltage). As the result of the forward voltage being lower than the electroluminescence turn-on voltage, the intensity of the electroluminescence signal is also low. As shown in equivalent circuit 192 of FIG. 1G, in time interval 175, the p-n junction capacitance Cpn is charged to steady conditions of charge Qpn, where the injection current compensates photocurrent, such that $J_{INJ}=J_{PH}$, $V_F>V_{EL}$ and electroluminescence is high. As shown in equivalent circuit 194 of FIG. 1H, in time interval 176 the output of the illumination source is off (i.e., excitation light is off), however the injection current $J_{INJ}$ continues to stimulate electroluminescence, while the charge Qpn on the p-n junction discharges.

In one embodiment, the system 100 may serve to monitor time- and space-resolved luminescence in order to extract the electroluminescence component of the total luminescence signal. In addition, system 100 may also monitor JPV signals, allowing the measurement of the internal quantum efficiency of the LED structure 103. As shown in FIG. 1E, the optical generation 186 of electrons and holes in LED structures 103 may lead to their confinement in quantum wells and direct photoluminescence, $I_{PL}$. Alternatively, separation of the electrons and holes by an electric field in the active layer, induces a p-n junction forward bias and injection of holes from the p-layer and electrons from the n-layer into quantum wells or an active area, thereby inducing non-contact electroluminescence $I_{EL}$ 189.

In order to increase the contribution of noncontact electroluminescence, and thus the ratio of the electroluminescence signal to the photoluminescence signal ($I_{EL}/I_{PL}$), the wavelength of light used to stimulate the LED structure may be in the range corresponding with maximum optical carrier collection. Further, pulse duration and diameter of the light beam and luminescence collection area may be optimized to maximize the steady state open circuit voltage or the forward voltage, thereby maximizing the resulting injection current.

In one embodiment, electroluminescence monitoring may include uniform illumination of an illumination area 118 of a wafer (e.g., LED structure 103), providing a uniform JPV signal inside of area 124 and a time-resolved deconvolution of direct photoluminescence, $I_{PL}$, and a non-contact electroluminescence, $I_{EL}$, from the area 124 based on the time intervals 174, 175 and 176 (shown in FIG. 1C).

It is noted herein that the total luminescence signal ($I_T$) is equal $I_T=I_{PL}+I_{EL}$. As shown in FIG. 1B, the contribution of electroluminescence may be increased and measured by collection of luminescence in the middle of illumination area 118, with r<<r1. Electroluminescence intensity, $I_{EL}$, can be determined by applying pulsed excitation illumination 171 (with a time duration such that $\tau_{EX}>\tau_{JPV}$) and determination of electroluminescence intensity $I_{EL}$ as a difference between luminescence intensities of impulse 173 at a first time interval of $\tau_{JPV}<t<\tau_{EX}$ (where intensity $I_T=I_{PL}+I_{EL}$) and a second time interval of $0<t<\tau_{JPV}$ (where $I_T\cong I_P$ when contribution of $I_{EL}$ is low).

In another embodiment, the electroluminescence intensity $I_{EL}$ may be determined using the luminescence decay 176 at $t>\tau_{EX}$. In this regard, upon the termination of the excitation from illumination source 110, the photoluminescence component of the luminescence signal becomes negligible due to the rapid decay of the PL signal (e.g., decay in nanosecond regime). In this regard, the electroluminescence intensity $I_{EL}$ may be identified as a value (e.g., maximum value) of EL at some selected time $t>\tau_{EX}$ after excitation light is off.

In another embodiment, the electroluminescence intensity $I_{EL}$ may be determined by applying a pulsed illumination 171 with duration $\tau_{EX}>\tau_{JPV}$, where the junction photovoltage based forward voltage $V_F$ is greater than the electroluminescence turn-on voltage $V_{EL}$, while also applying pulsed illumination with the same intensity but lower duration $\tau_{Ex}<\tau_{JPV}$, such that the forward voltage $V_F$ is less than the electroluminescence turn-on voltage $V_{EL}$. Then, the electroluminescence intensity $I_{EL}$ may be calculated as a difference of the above luminescence amplitudes. For example, in the case of GaInN LED structures, an appropriate turn-on voltage may be approximately $V_{EL}=2.3V$.

In another embodiment, the JPV forward voltage, $V_F$, may be determined by measuring the JPV signal 172 picked up by a transparent electrode 144. To accelerate JPV decay and provide accurate measurement of JPV forward voltage p and n layers may be electrically connected using spring loaded electrode 156 and conducting pads 154a, 154b, as shown in FIG. 1A.

Photocurrent density, $J_L$, can be determined via the derivative of the JPV transient, V(t), represented by the line 178 tangential to the front portion of the JPV signal 172. For example, the controller 108 may determine the photocurrent density using the following relationship:

$$J_L = C_{pn}\frac{dJPV(t)}{dt} \tag{1}$$

where $C_{pn}$ is the capacitance of the p-n junction of the LED structure 103. In the case of p-i-n structures (e.g., InGaN-based LED emitters) a junction capacitance is given by $C_{pn}=\in_S\in_0/d$, where d is a thickness of the active i-layer, $\in_S$, $\in_0$ are dielectric permittivity of semiconductor and the vacuum medium respectively. As such, the electroluminescence internal quantum efficiency (IQE) or $\eta_{EL}$ can be calculated by the controller 108 using the following relationship:

$$\eta_{EL}=\frac{I_{EL}}{V_FJ_L} \tag{2}$$

Here, the electroluminescence IQE is determined by carrier injection efficiency and radiative efficiency in active layers of LED structures (e.g., quantum wells in GaInN LEDs). In this regard, the electroluminescence IQE is related to the injection efficiency and radiation efficiency as follows:

$$\eta_{EL}=\eta_{injection}\eta_{radiative} \tag{3}$$

Further, the controller 108 may determine the photoluminescence efficiency via photocarrier collection and radiative efficiency in an active layer with the following relationship:

$$\eta_{PL}=\eta_{PL\_collect}\eta_{radiative} \tag{4}$$

In addition, using the electroluminescence intensities and the electroluminescence internal quantum efficiency $\eta_{EL}$ the controller 108 may approximate the electroluminescence injection efficiency by:

$$\eta_{injection}\approx\eta_{EL}\frac{I_{EL}}{I_{PL}} \tag{5}$$

It is noted herein that the system 100 is not limited to calculating the various characteristics of the LED structure 103, as described previously herein, using the equations and relationships provided above. The various equations and relationships provided in the present disclosure are provided merely for illustrative purposes and should not be interpreted as limitations on the present disclosure. It is recognized herein that various relationships may be utilized by the controller 108 to relate two or more of the previously described quantities within the scope and spirit of the present invention.

Figure 2A:
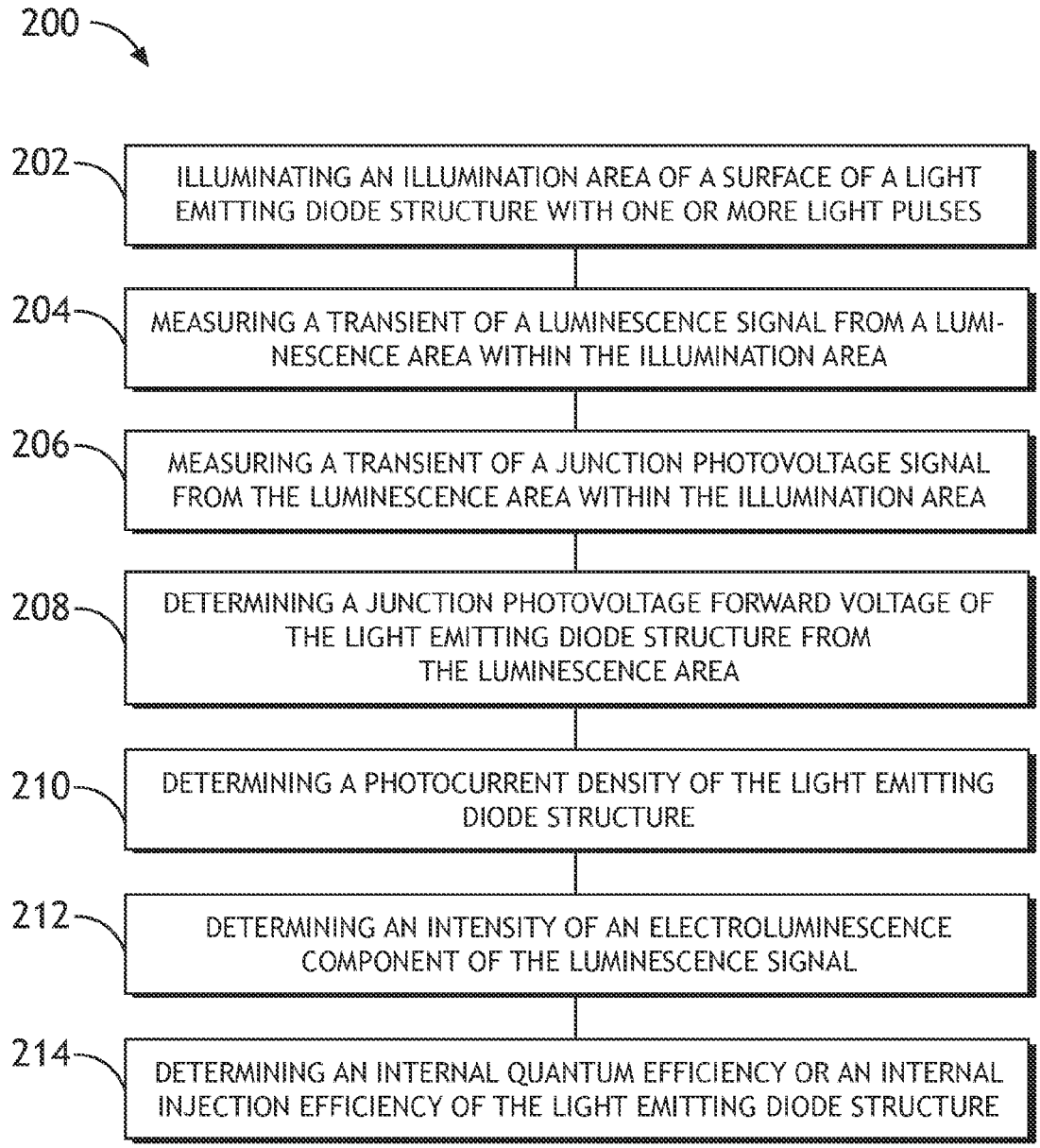
FIG. 2A is a flow diagram illustrating a method for contactless measurement of one or more characteristics of a LED structure, in accordance with one embodiment of the present disclosure.

FIG. 2A illustrates a flow diagram depicting a method 200 for contactless measurement of one or more characteristics of a LED structure, in accordance with one or more embodiments of the present disclosure. It is recognized herein that one or more of the steps of the method 200 may be implemented by one or more of the components and embodiments of system 100. It is noted, however, that method 200 is not limited to the structural limitations of system 100.

Step 202 illuminates an illumination area of a surface of a light emitting diode structure with one or more light pulses. For example, the controller 108 may direct he illumination source 110 to illuminate a selected illumination area 118 of the surface of a LED structure 103 with excitation illumination having one or more light pulses of selected amplitude and/or duration.

Step 204 measures a transient of a luminescence signal from a luminescence area within the illumination area with a luminescence sensor. For example, the sensor 122 may acquire luminescence light that is emitted by the LED structure 103 in response to the excitation illumination. Further, various optical elements, as described previously herein, may be used to limit the area of luminescence collection to an area 124 smaller than the illumination area 118.

Step 206 measures a transient of a junction photovoltage signal from the luminescence area within the illumination area. For example, the transparent electrode 144 may be positioned within the illumination area 118 and proximate to the surface of the light emitting diode structure 103, allowing the transparent electrode 144 to measure the junction photovoltage transient from the area 124 subtended by the transparent electrode 144.

Step 208 determines a junction photovoltage forward voltage of the light emitting diode structure from the luminescence area. In one embodiment, the controller 108 may determine the junction photovoltage forward voltage based on the amplitude of the junction photovoltage signal measured from the illumination area 118 with the transparent electrode 144. For example, the controller 108 may identify JPV forward voltage $V_F$ as being the amplitude of the junction photovoltage signal measured from the illumination area 118.

Step 210 determines a photocurrent density of the light emitting diode structure. In one embodiment, the controller 108 may determine the junction photovoltage $J_L$ by calculating the derivative (e.g., using equation (1)) of the transient of the JPV signal at a front edge of the JPV signal. In another embodiment, the controller 108 may acquire (e.g., user input, calculation or independent measurement) a capacitance $C_{PN}$ of a p-n junction of the LED structure 103. In another embodiment, the controller 108 may calculate the photocurrent density $J_L$ of the LED structure 103 with the derivative of the transient of the JPV signal and the capacitance of the p-n junction of the LED structure 103.

Step 212 determines an intensity of an electroluminescence component of the luminescence signal. It is noted herein that the electroluminescence component of the luminescence signal may be determined in any manner described throughout the present disclosure. In one embodiment, the EL component of the luminescence is found by identifying a first time interval corresponding with the junction photovoltage forward voltage $V_F$ being lower than a turn-on voltage $V_{EL}$ of the electroluminescence signal based on the transient of the junction photovoltage. Then, a second time interval may be identified corresponding with the junction photovoltage forward voltage $V_F$ being higher than the turn-on voltage $V_{EL}$ of the electroluminescence signal based on the transient of the junction photovoltage. Then, the intensity of the electroluminescence component ($I_{EL}$) of the luminescence signal is determined by calculating a difference between a first luminescence signal acquired during the second time interval and a second luminescence signal acquired during the first time interval and the fact that the total luminescence signal is given by $I_T=I_{EL}+I_{PL}$. As such, a difference between two luminescence intensities, when IPL is relatively constant and one of the states includes is below the EL turn-on voltage, yields the $I_{EL}$ value in the turned-on state.

In another embodiment, upon terminating the illumination of the light emitting diode structure, the EL component of the luminescence is found by identifying a value of the luminescence signal following a selected time of decay of the luminescence signal. In this regard, the PL component of the luminescence decay rapidly (on the order of nanoseconds) following the termination of the excitation illumination from the illumination source 110. As such, the EL component may be identified by measuring luminescence with sensor 122 at a selected time almost immediately following illumination shut-off. It is noted herein that the controller 108 may utilize a time of EL acquisition that allows for sufficient PL component decay.

In another embodiment, the EL component of the luminescence is found by establishing a duration time of the one or more light pulses so as to illuminate the illumination area with a first one or more light pulses having a first duration sufficient to establish a steady-state condition when forward voltage is higher than electroluminescence turn-on voltage. Then, a duration time of the one or more light pulses is established so as to illuminate the illumination area with a second one or more light pulses having a second duration shorter than the first duration and sufficient to establish a non-steady state condition when the forward voltage is lower than electroluminescence turn-on voltage. In another embodiment, the intensity of the electroluminescence signal component is determined by calculating the difference between a first luminescence intensity acquired during illumination with the first one or more light pulses and a second luminescence intensity acquired during illumination with the second one or more light pulses.

Step 214 determines the internal quantum efficiency or the internal injection efficiency of the light emitting diode structure. In one embodiment, the controller 108 may determine the internal quantum efficiency IQE or the internal injection efficiency using the determined junction photovoltage forward voltage $V_F$ of the LED structure 103 from the illumination area 118, the photocurrent density $J_L$ of the LED structure 103 or the intensity of the electroluminescence component $I_{EL}$ of the luminescence signal measured by sensor 122.

Figure 2B:
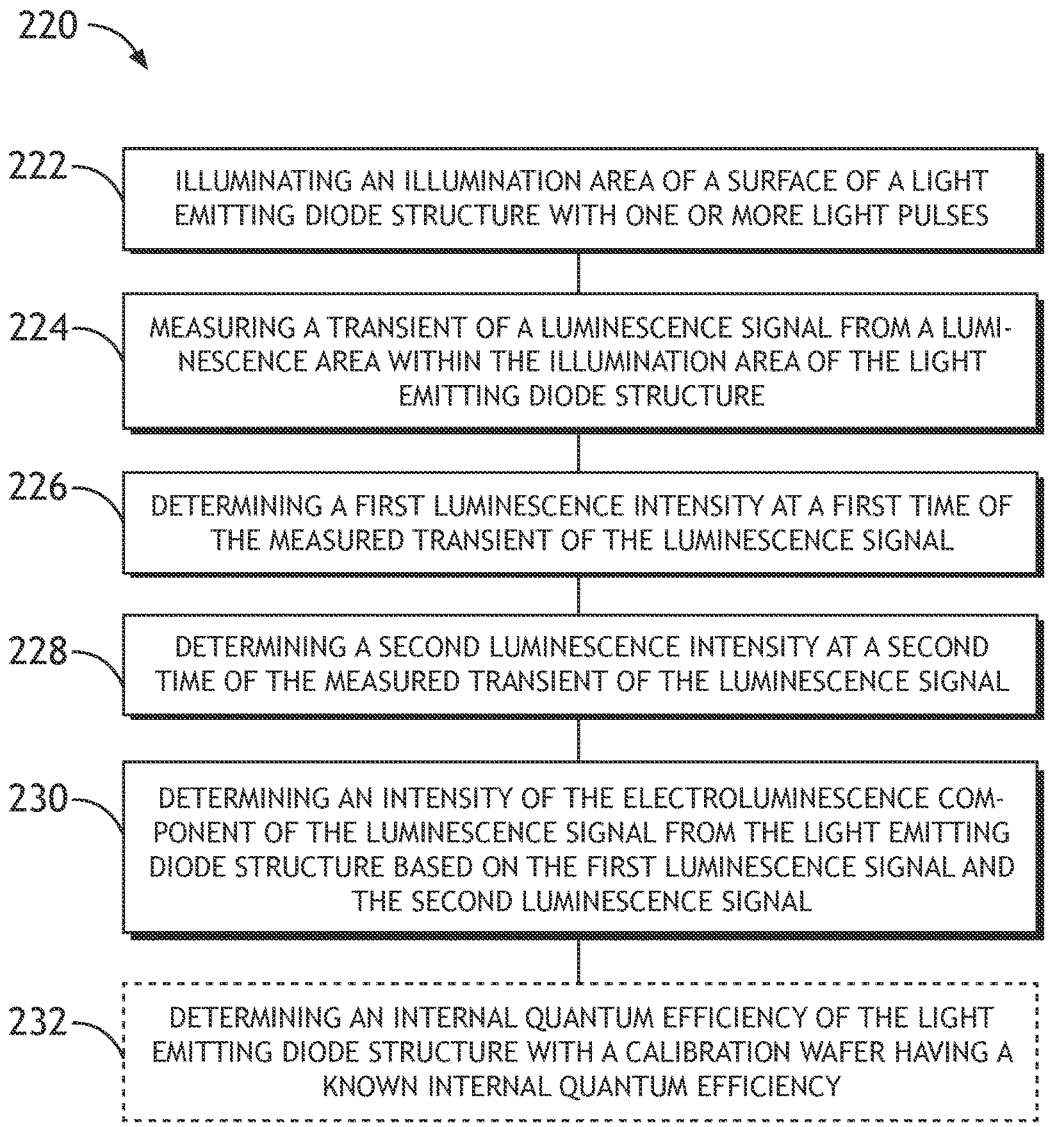
FIG. 2B is a flow diagram illustrating a method for contactless measurement of one or more characteristics of a LED structure, in accordance with one embodiment of the present disclosure.

FIG. 2B illustrates a flow diagram depicting a method 220 for contactless measurement of one or more characteristics of a LED structure, in accordance with one or more embodiments of the present disclosure. It is recognized herein that one or more of the steps of the method 220 may be implemented by one or more of the components and embodiments of system 100. It is noted, however, that method 220 is not limited to the structural limitations of system 100.

Step 222 illuminates an illumination area 118 of a surface of a light emitting diode structure 103 with one or more light pulses, as described previously herein.

Step 224 measures a transient of a luminescence signal from a luminescence area 124 within the illumination area 118 of the LED structure 103 with a luminescence sensor 122, as described previously herein.

Step 226 determines a first luminescence intensity at a first time of the measured transient of the luminescence signal from the LED structure 103. For example, the controller 108 may determine a first luminescence intensity at a first time of the measured transient of the luminescence signal (e.g., a first time of transient signal 173 in FIG. 1C) from the LED structure 103.

Step 228 determines a second luminescence intensity at a second time different from the first time of the measured transient of the luminescence signal from the LED structure 103. For example, the controller 108 may determine a second luminescence intensity (or an Nth time) at a second time (or an Nth time) of the measured transient of the luminescence signal (e.g., a second time of transient signal 173 in FIG. 1C) from the LED structure 103.

Step 230 determines an intensity of the electroluminescence component of the luminescence signal from the light emitting diode structure based on the first luminescence intensity and the second luminescence intensity. For example, the controller 108 may determine an intensity amplitude of the electroluminescence component of the luminescence signal from the LED structure 103 my comparing the first luminescence intensity to the second luminescence intensity (e.g., calculating a difference, calculating a ratio, fitting to each intensity to a mathematical model and the like).

Step 232 determines an internal quantum efficiency of the LED structure 103 with a calibration wafer having a known internal quantum efficiency. In one embodiment, the determination of the IQE of the LED structure 103 with a calibration includes illuminating an illumination area of a surface of a calibration wafer having a known internal quantum efficiency with one or more light pulses. Then, a transient of a luminescence signal is measured from a luminescence area within the illumination area of the calibration wafer with a luminescence sensor. Then, a first luminescence intensity at a first time of the measured transient of the luminescence signal is measured from the calibration wafer. Then, a second luminescence intensity at a second time different from the first time of the measured transient of the luminescence signal is measured from the calibration wafer. Then, an intensity of the electroluminescence component of the luminescence signal from the calibration wafer is determined based on the first luminescence signal and the second luminescence signal. Then, the IQE of the LED structure 103 is determined using the intensity of electroluminescence component from the light emitting diode structure, the intensity of the electroluminescence component from the calibration wafer and the known IQE of the calibration wafer.

Figure 2C:
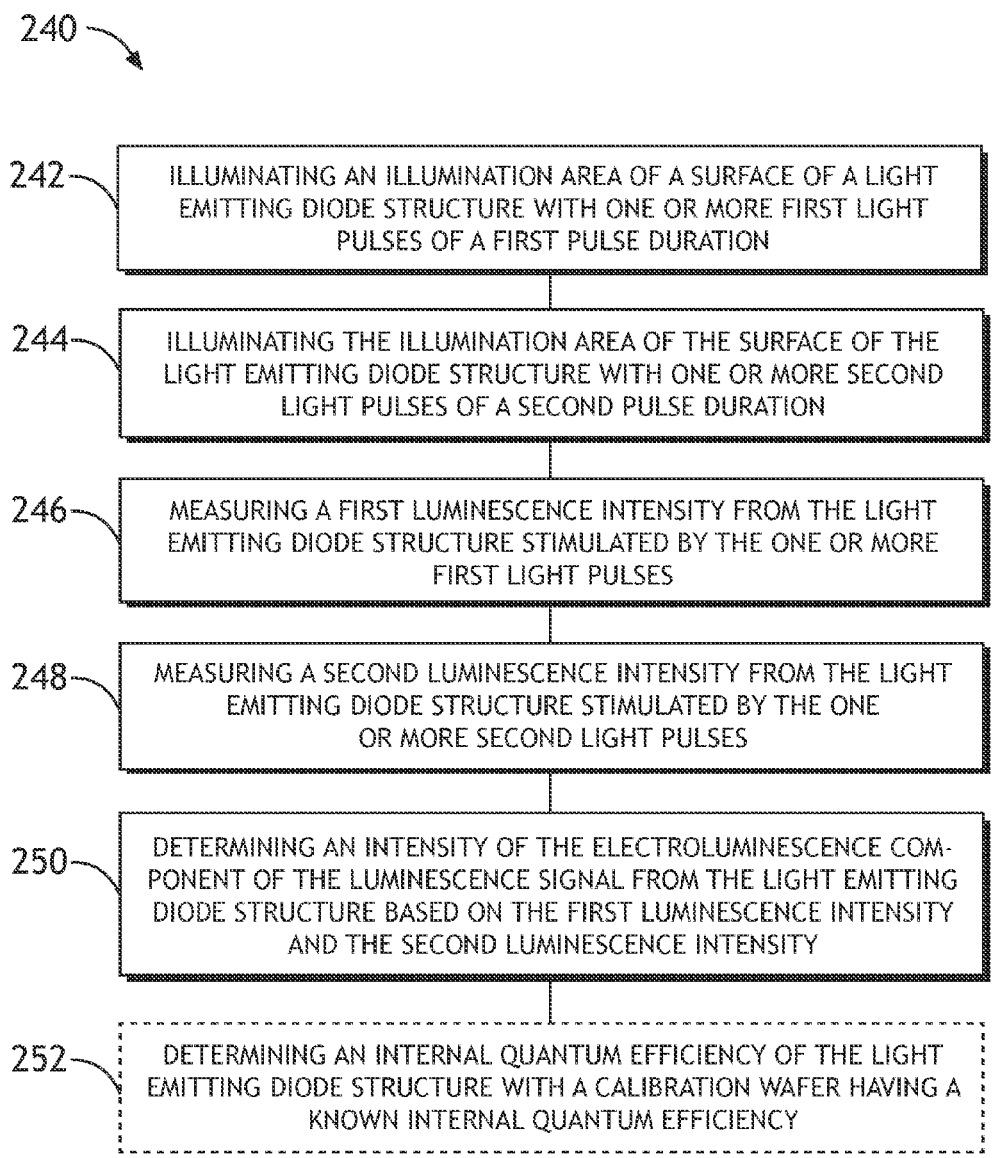
FIG. 2C is a flow diagram illustrating a method for contactless measurement of one or more characteristics of a LED structure, in accordance with one embodiment of the present disclosure.

FIG. 2C illustrates a flow diagram depicting a method 240 for contactless measurement of one or more characteristics of a LED structure, in accordance with one or more embodiments of the present disclosure. It is recognized herein that one or more of the steps of the method 240 may be implemented by one or more of the components and embodiments of system 100. It is noted, however, that method 240 is not limited to the structural limitations of system 100.

Step 242 illuminates an illumination area 118 of a surface of a light emitting diode structure 103 with one or more first light pulses of a first pulse duration. For example, the controller 108 may direct the illumination source 110 to illuminate the LED structure 103 with a first light pulse of a first pulse duration.

Step 244 illuminates the illumination area of the surface of the light emitting diode structure with one or more second light pulses of a second pulse duration. For example, the controller 108 may direct the illumination source 110 to illuminate the LED structure 103 with a second light pulse of a second pulse duration.

Step 246 measures a first luminescence intensity from the light emitting diode structure stimulated by the one or more first light pulses. For example, the optical sensor 122 may measure a first luminescence intensity from the LED structure 103 stimulated by the first light pulse.

Step 248 measures a second luminescence intensity from the light emitting diode structure stimulated by the one or more second light pulses. For example, the optical sensor 122 may measure a second luminescence intensity from the LED structure 103 stimulated by the second light pulse.

Step 250 determines an intensity of the electroluminescence component of the luminescence signal from the light emitting diode structure based on the first luminescence intensity and the second luminescence intensity. For example, the controller 108 may determine an intensity amplitude of the electroluminescence component of the luminescence signal from the LED structure 103 my comparing the first luminescence intensity to the second luminescence intensity (e.g., calculating a difference, calculating a ratio, fitting to each intensity to a mathematical model and the like).

Step 252 determines an internal quantum efficiency of the LED structure 103 with a calibration wafer having a known internal quantum efficiency. In one embodiment, the determination of the IQE of the LED structure 103 using a calibration wafer includes illuminating an illumination area of a surface of a calibration wafer with a known internal quantum efficiency with one or more first light pulses of a first pulse duration. Then, the illumination area of the surface of the calibration wafer is illuminated with one or more second light pulses of a second pulse duration. Then, the first luminescence intensity from the calibration wafer stimulated by the one or more first light pulses is measured. Then, a second luminescence intensity from the calibration wafer stimulated by the one or more second light pulses is measured. Then, an intensity of the electroluminescence component of the luminescence signal from the calibration wafer is determined based on the first luminescence intensity and the second luminescence intensity. Then, the IQE of LED structure 103 is determined with the intensity of electroluminescence component from the light emitting diode structure, the intensity of the electroluminescence component from the calibration wafer and the known IQE of the calibration wafer.

Referring now to FIGS. 3A-3G, in one embodiment, the system 100 is arranged to measure electroluminescence from a shadowed region 304. It is noted herein that the components, steps and embodiments described previously herein are interpreted to extend to the implementation of system 100 depicted in FIGS. 3A-3G, unless otherwise noted.

In one embodiment, the system 100 may serve to monitor electroluminescence in LED structures 103 with low sheet resistance of the top window layer, as depictured further herein. Such measurements may be based on optical excitation of an area (caused by illumination of the area with light 307) of a LED structure 103 with the intensity modulated light and the monitoring of electroluminescence and JPV signals outside of the illuminated area.

Figure 3A:
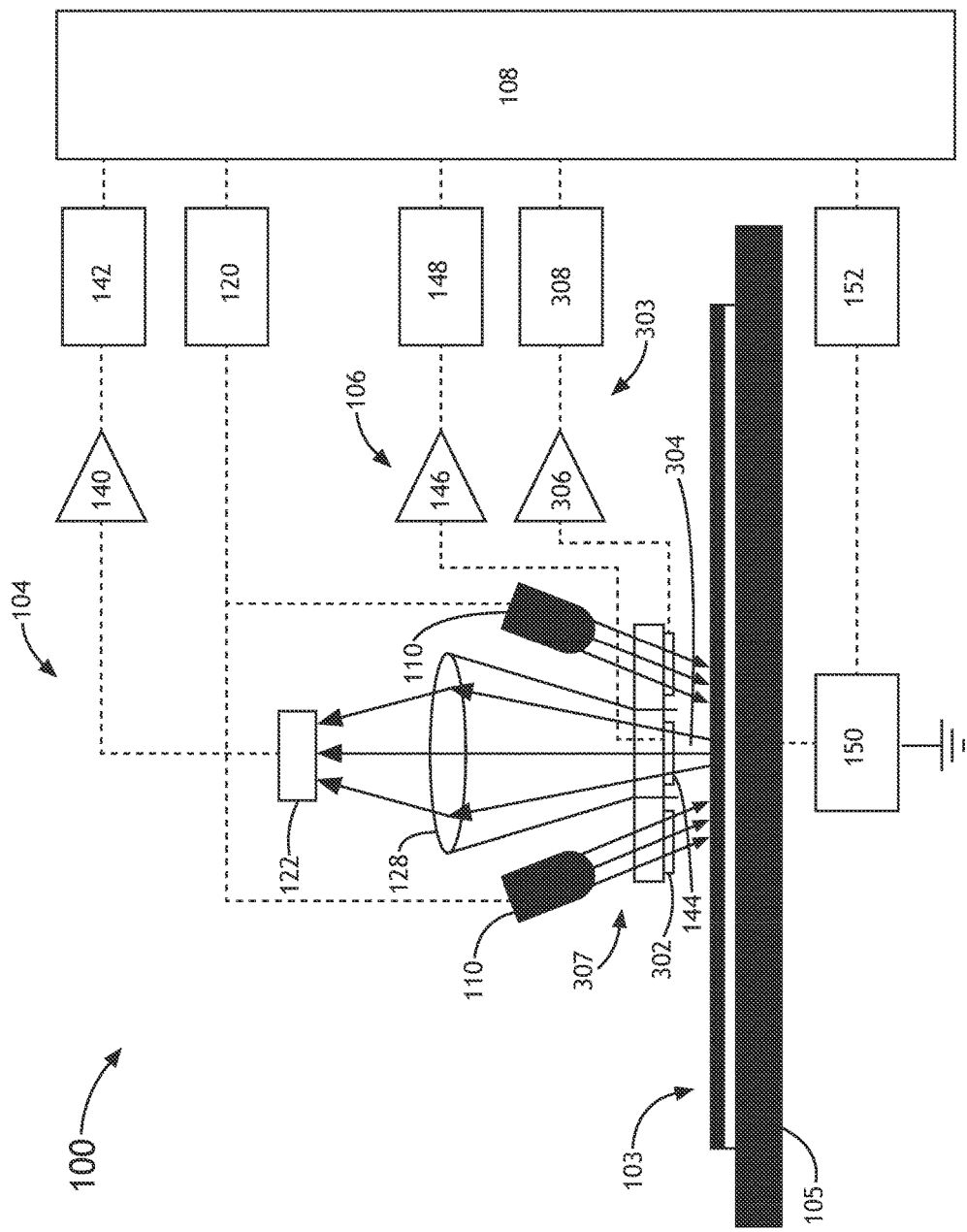
FIG. 3A is a block diagram illustrating an apparatus for contactless measurement of one or more characteristics of a LED structure, in accordance with one embodiment of the present disclosure.

The basis of this measurement process depicted in FIG. 3A, and related figures, includes the monitoring of spatially resolved electroluminescence induced by a photoluminescence excitation. Electroluminescence induced by photoluminescence excitation and electrical drift of excess carriers outside of an illumination area has been observed by M. F. Shubert in such structures as GaInN/GaN LED structures in *Electroluminescence Induced by Photoluminescence Excitation in GaInN/GaN Light Emitting Diodes, Appl. Phys. Lett.*, 95, 191105 (2009), which is incorporated herein by reference in the entirety. The electrical drift current stimulated by spreading photo generated electron-holes pairs outside of illumination area has described by V. Faifer et. al. in *Proceedings of 24th ESSDERC'94, Edinburgh*, p. 601 (1994), which is incorporated herein by reference in the entirety.

In one embodiment, the illumination source 110 may include a ring illumination source, as shown in FIG. 3A. In this regard, the illumination source 110 may illuminate a ring-shaped illumination area, which surrounds a central region probed by the first transparent electrode 144. In this regard, the central portion of the LED structure 103 is shadowed in that it is unexposed by the illumination 307 from the illumination source 110. It is noted herein that in this embodiment the illumination source 110 is not limited to a ring shape and may take on any suitable shape known in the art, such as but not limited to, a circular ring, a square ring, a polygonal ring, an oval ring and the like. Further, the illumination source 110 may be formed from multiple illumination sources that serve to discretely (e.g., series of illumination spots) or continuously form an illumination pattern on the LED structure 103 that surrounds the shadowed region 304.

In another embodiment, the first transparent electrode of the first junction photovoltage measurement unit 106 measures an unexposed junction photovoltage signal from the unexposed, or shadowed region 304, of the light emitting diode structure 103.

In another embodiment, the system 100 includes a second junction photovoltage measurement unit 303 including a second transparent electrode 302 positioned proximate to the LED structure 103. In one embodiment, the second transparent electrode 302 encompasses the first transparent electrode 144. In another embodiment, second transparent electrode 302 measures an exposed junction photovoltage signal from the illumination area of the LED structure 103 external to the first transparent electrode 144.

In one embodiment, the second transparent electrode 302 may be arranged concentrically with respect to the first transparent electrode 144, as shown in FIG. 3A. For example, the second transparent electrode 302 may have a ring shape. For instance, the first electrode 144 may have a circular disk shape, while the second electrode 302 has a circular ring shape that surrounds the central first electrode 144. It is noted herein that the second transparent electrode 302 is not limited to a circular ring shape and may take on any suitable shape known in the art, such as but not limited to, a circular ring, a square ring, a polygonal ring, an oval ring and the like.

In another embodiment, the second junction photovoltage measurement unit 303 includes one or more signal processing elements. For example, the second junction photovoltage measurement unit 303 may include, but is not limited to, a preamplifier 306 or a demodulator and/or detector 308, which is coupled to the controller 108.

In another embodiment, the optical sensor 122 of the luminescence measurement unit 104 measures an electroluminescence intensity from the shadowed region 304 of the LED structure 103 unexposed to the intensity modulated light from the illumination source 110.

In another embodiment, the controller 108 is communicatively coupled to the luminescence measurement unit 104, the first junction photovoltage measurement unit 106, the second junction photovoltage measurement unit 303, as well as the illumination unit 102. In this regard, the controller 108 may receive measurement results from the various devices of the system 100 and provide various control functions and measurement output results, in a manner similar to that described previously herein. In one embodiment, the controller 108 controls one or more characteristics of the light 307 from the illumination source 110. In another embodiment, the controller 108 receives one or more measurements of the electroluminescence signal from the luminescence measurement unit 104 (e.g., optical sensor 122 of unit 104). In another embodiment, the controller 108 receive one or more measurements of the unexposed junction photovoltage signal from the first junction photovoltage measurement unit 106 (e.g., first transparent electrode 144 of the junction photovoltage measurement unit 106). In another embodiment, the controller 108 receives one or more measurements of the exposed junction photovoltage signal from the second junction photovoltage measurement unit 303 (e.g., second transparent electrode 302 of the junction photovoltage measurement unit 303). In another embodiment, as described further herein, the controller 108 determines a photocurrent density $J_L$ of the LED structure 103 using the measured unexposed junction photovoltage signal (from unit 106) and the measured exposed junction photovoltage (from unit 303). In another embodiment, as described further herein, the controller 108 determine a forward voltage $V_F$ of the LED structure 103 based on one or more additional junction photovoltage measurements from the first transparent electrode 144 and one or more additional junction photovoltage measurements from the second transparent electrode 302. In another embodiment, as described further herein, the controller 108 determine an IQE of the LED structure 103 using one or more of the measured electroluminescence intensity from the shadowed region 304 of the LED structure 103, the determined photocurrent density $J_L$ of the LED structure 103 or the determined forward voltage $V_F$ of the LED structure 103.

Figure 3B:
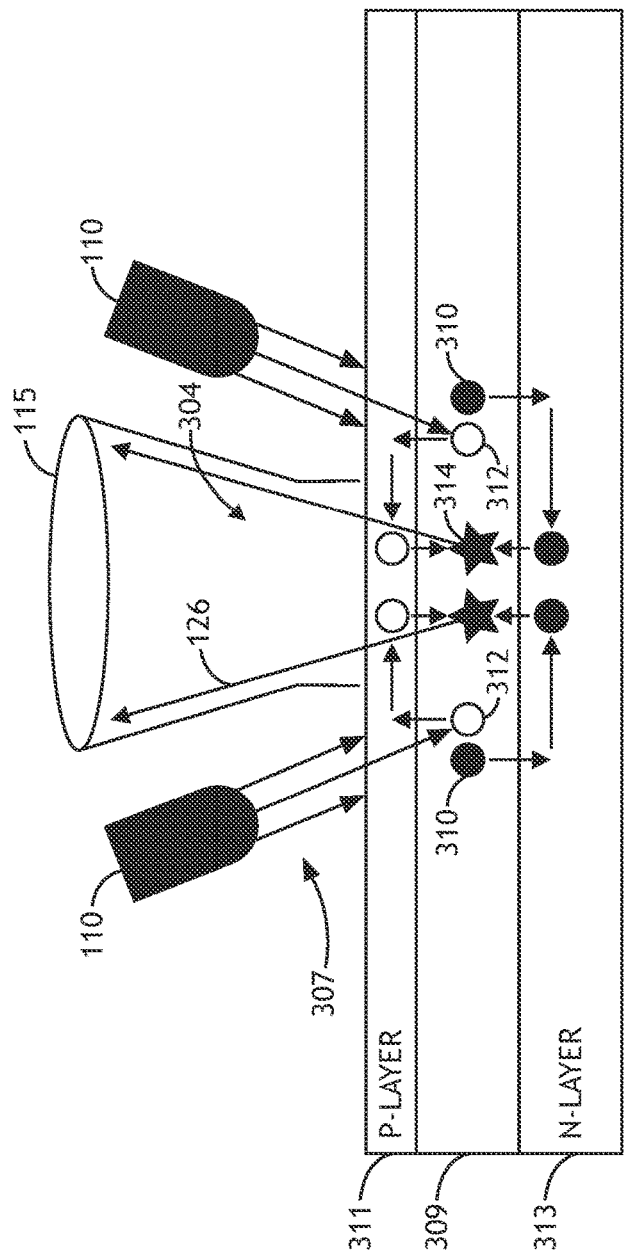
FIG. 3B is a conceptual view of the mechanisms involved in electroluminescence generation, in accordance with one embodiment of the present disclosure.

FIG. 3B depicts a conceptual view of the mechanisms involved in electroluminescence generation, in accordance with one embodiment of the present disclosure. In one embodiment, the illumination source 110 generates electrons 310 and holes 312 within an active layer 309 outside of shadowed region 304. Further, an electric field separates said electrons 310 and holes 312 and moves them towards the n-layer 313 and p-layer 311. Then, the carriers drift laterally into the shadowed region 304. In addition, excess electrons and holes in shadowed region 304 generate a forward bias, with the electrons 310 and holes 312 being injected into the active layer 309. The electron and holes then recombine and electroluminescence 314 is generated and may be, but is not required to be, collected by a lens 115, resulting in an EL signal output 126.

In one embodiment, as noted previously herein, the system 100 may monitor electroluminescence via the illumination of the area outside of shadowed area 304 of the LED structure 103 and collection and detection of electroluminescence from the shadowed area 304 using a lens 115 and sensor 122. In one embodiment, the internal quantum efficiency may be determined by measuring the forward voltage $V_F$ and injection current $J_L$ using a transparent electrode 144. In another embodiment, the forward voltage can be measured by applying a light pulse from the illumination source 110 with the same intensity as a photoluminescence signal and measuring an amplitude of the forward voltage based on a JPV signal acquired with transparent electrode 144. It is noted herein that the photocurrent density $J_L$ may be measured by using JPV signals picked up by electrodes 144, $V_1$, and 302, $V_2$, and the following relationship:

$$J_L \approx \frac{\pi(r_1 + r_2)}{R_S} \frac{(V_1/S_1 - V_2/S_2)}{r_1 - r_2} \quad (6)$$

Where $S_1$, $r_1$ and $S_2$, $r_2$ represent areas and radii of the inner electrode 144 and second transparent electrode 302 respectively (in a circular geometry) and $R_S$ represents the sheet resistance of the top layer of the LED structure 103. As noted previously herein, the electroluminescence IQE may be determined using the electroluminescence intensity $I_{EL0}$, the forward voltage, $V_F$, photocurrent, $J_L$, and formula (2) provided above.

Figure 3C:
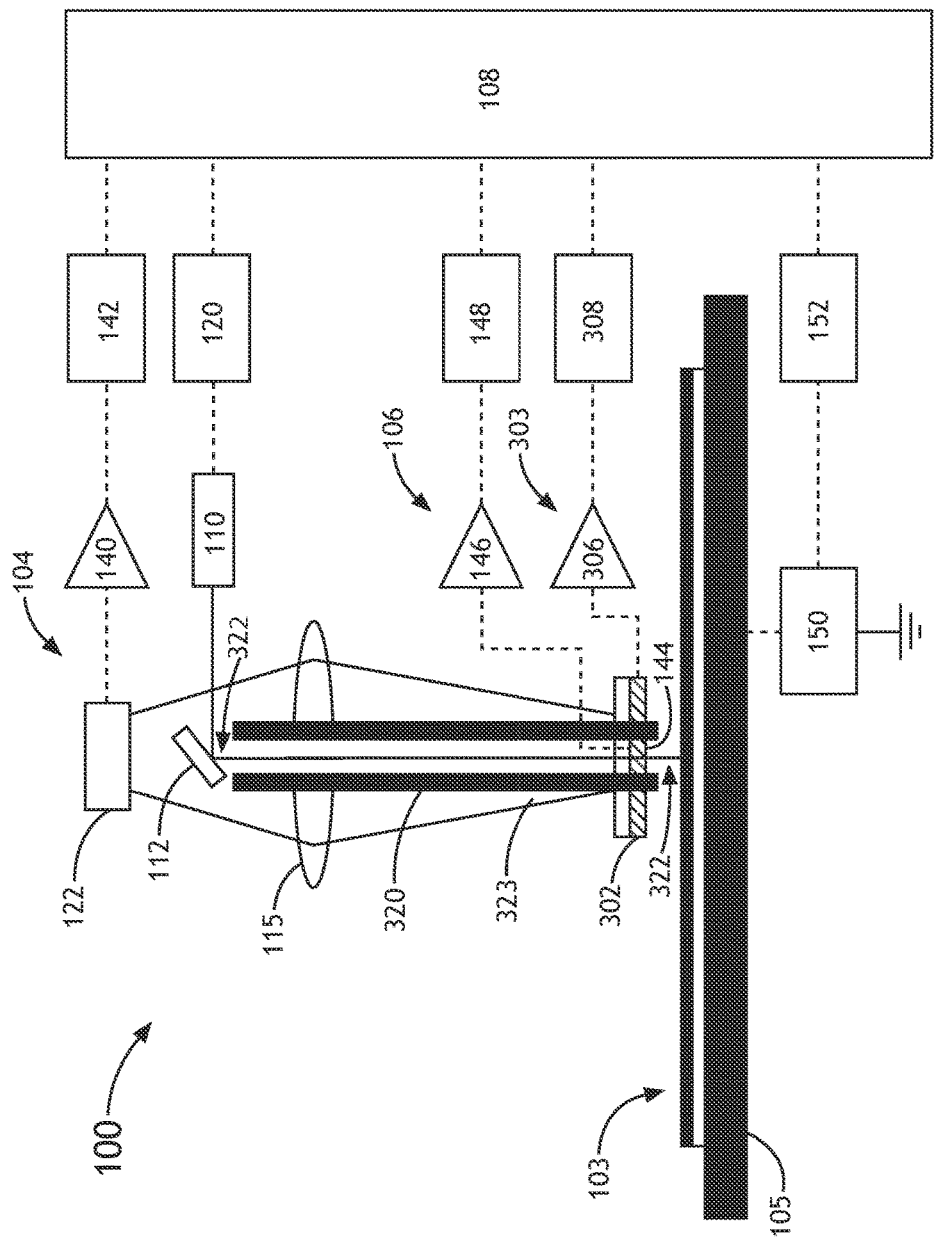
FIG. 3C is a block diagram illustrating an apparatus for contactless measurement of one or more characteristics of a LED structure, in accordance with one embodiment of the present disclosure.
Figure 3D:
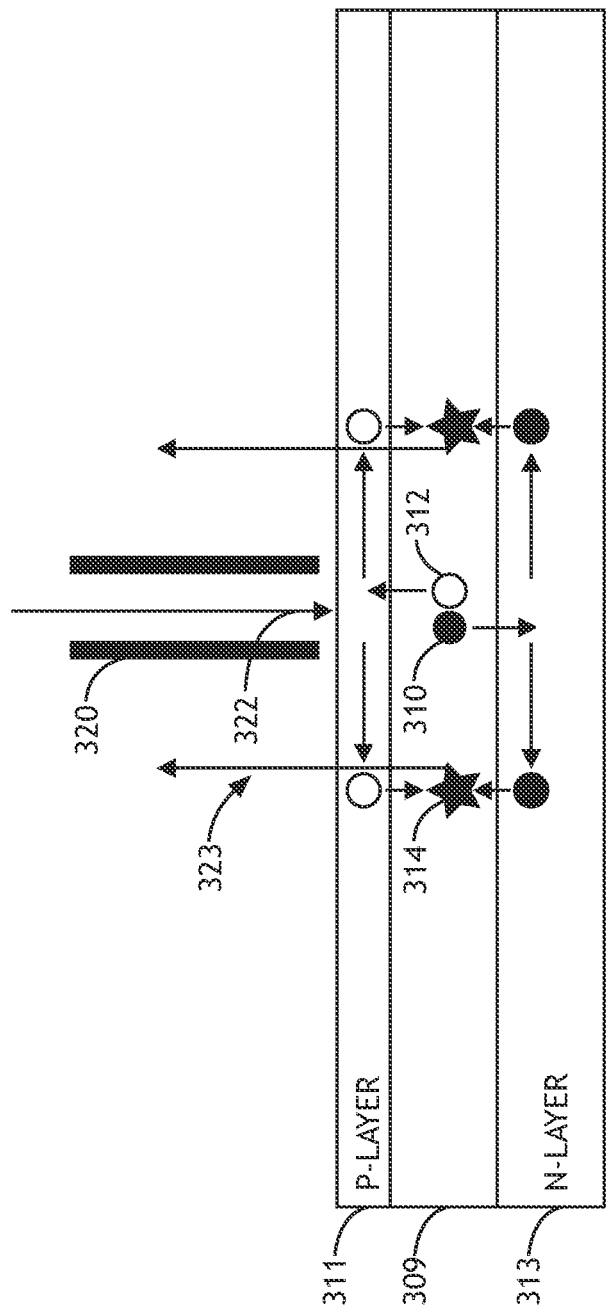
FIG. 3D is a conceptual view of the mechanisms involved in electroluminescence generation, in accordance with one embodiment of the present disclosure.

FIGS. 3C and 3D illustrate system 100 equipped with a tube structure 320, in accordance with one embodiment of the present disclosure. In one embodiment, the tube structure 320 is inserted through an opening passing through lens 115. The tube structure 320 serves to separate illumination from illumination source 110 from the stimulated electroluminescence illumination 323. In this regard, the tube structure 320 allows for the measurement of a JPV signal using the second transparent electrode 302 and the measurement of an electroluminescence signal 323, both outside of the illumination area 322. In one embodiment, the tube structure 320 may include a metal tube. In another embodiment, the tube structure 320 includes a non-metal tube.

FIG. 3D depicts a conceptual view of the mechanisms involved in the electroluminescence generation depicted in FIG. 3O, in accordance with one embodiment of the present disclosure. In one embodiment, the illumination source 110 generates electrons 310 and holes 312 within an active layer 309 inside of the illuminated area 322. Further, an electric field separates said electrons 310 and holes 312 and moves them towards the n-layer 310 and p-layer 311. Then, the carriers drift laterally outside of the illuminated area 322. In addition, excess electrons and holes outside of illumination area 322 generate a forward bias, with the electrons 310 and holes 312 being injected into the active layer 309. The electron and holes then recombine and electroluminescence 314 is generated and may be, but is not required to be, collected by a lens 115, which results in electroluminescence signal 323 (external to the tube structure 320).

In one embodiment, the system 100 may monitor electroluminescence via the illumination of the area 322 of the LED structure 103 under the first transparent electrode 144 and collection and detection of electroluminescence from the area outside of the exposed area 322 using a lens 115 and sensor 122. As previously noted herein, the tube structure 320 allows the system 100 to measure one or more JPV signals using a transparent electrode 144 and a second transparent electrode 302, with electroluminescence being collected outside of the illumination area 322 with the lens 115 and sensor 122.

It is again noted herein that photocurrent, $J_L$, can be measured using JPV signals picked up by electrodes 144, $V_1$, and 302, $V_2$, along with formula (6) provided above, where $S_1$, $r_1$ and $S_2$, $r_2$ represent the inner and outer areas and radii of electrodes 144 and 302 respectively and $R_S$ is a sheet resistance of the top layer 311. Further, electroluminescence IQE may be determined using electroluminescence intensity, $I_{EL0}$, forward voltage, $V_F$, photocurrent, $J_L$, and formula (2).

It is noted herein that the separation mechanism depicted in FIGS. 3C and 3D is not limited to the tube structure 320. Rather, any set of optical elements suitable for separating excitation illumination and the stimulated electroluminescence illumination 323 is suitable for implementation in the present invention. For example, an optical fiber coupled to the output of the illumination source 110 may be used to illuminate the area under transparent electrode 144, while avoiding exposure to the region outside of the transparent electrode 144 (under the second transparent electrode 302). It is noted herein that various types of fiber bundle combiners may be used for illuminating a first area and collecting electroluminescence from an area outside of the illuminated area.

Figure 3E:
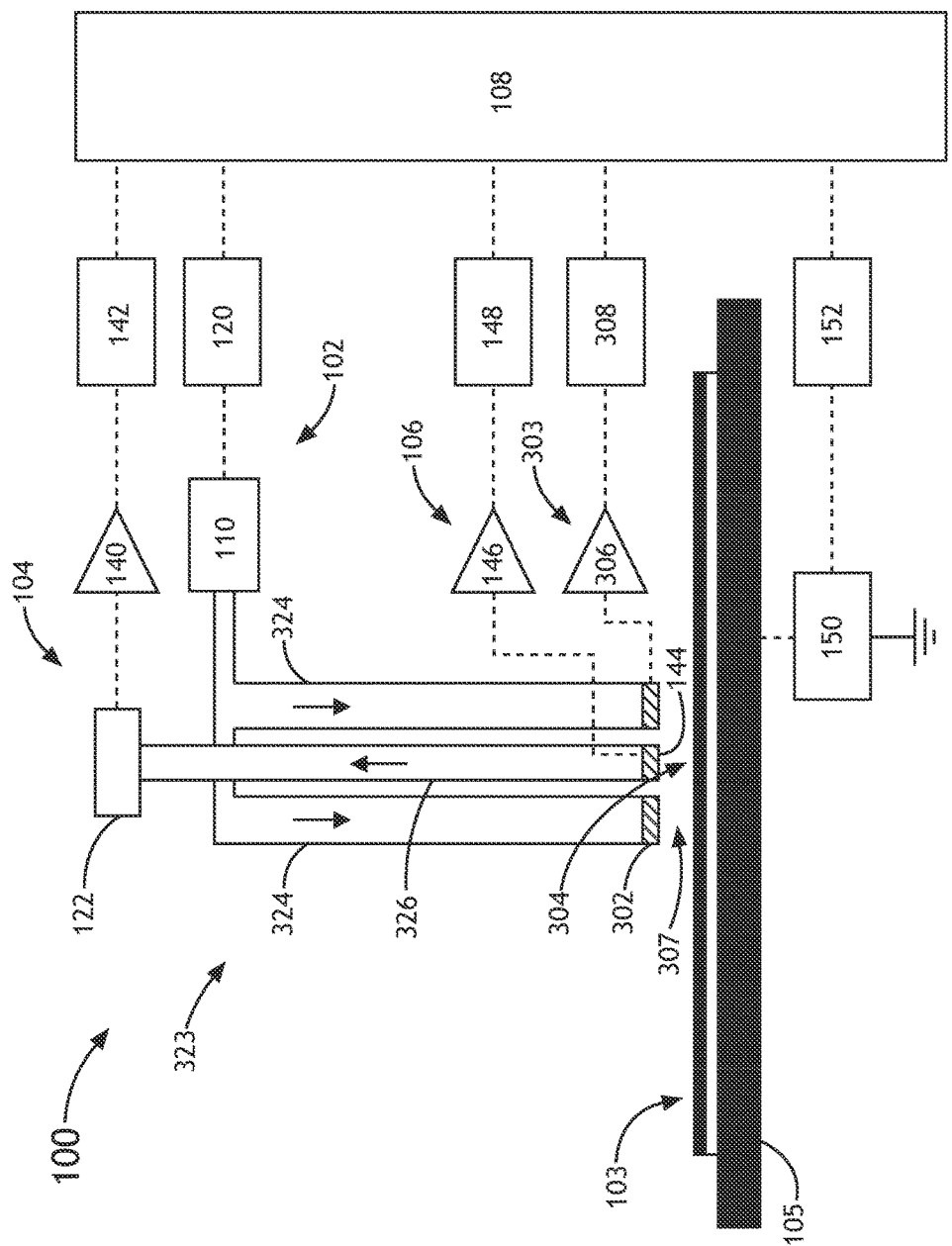
FIGS. 3E-3F illustrate an apparatus for contactless measurement of one or more characteristics of a LED structure, in accordance with one embodiment of the present disclosure.
Figure 3F:
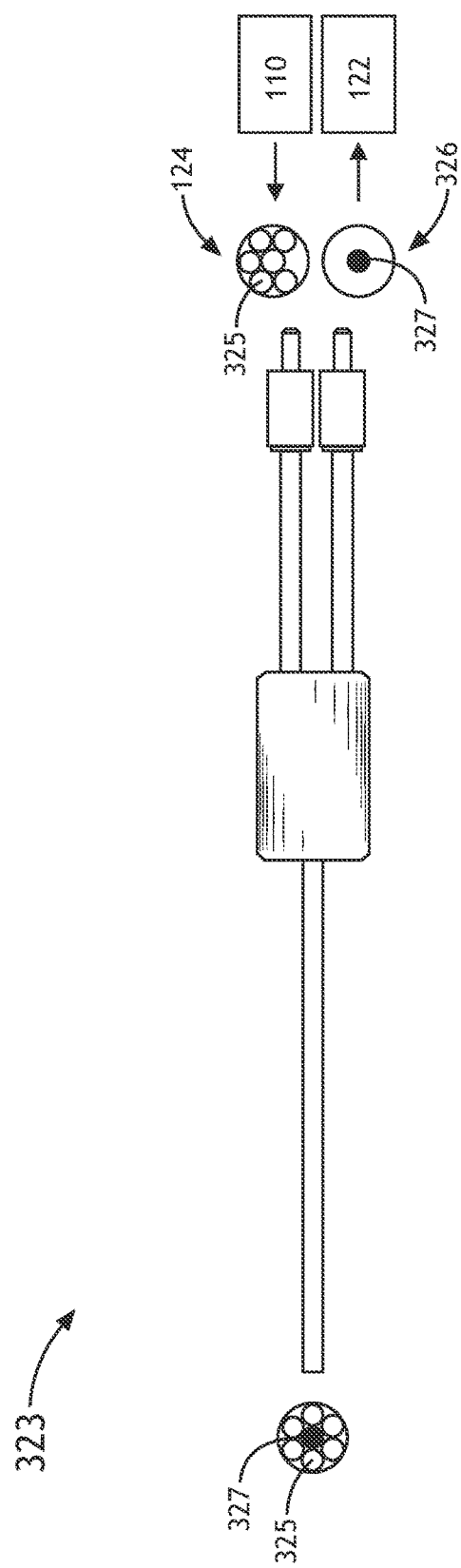

FIGS. 3E and 3F illustrate an optical probe 323 suitable for implementation in system 100 for separating illumination from the illumination source 110 and the resulting electroluminescence illumination. For example, as shown in FIG. 3E, the optical probe 323 may include an illumination channel 324 including one or more illuminating fibers 325 and a read channel 326 including one or more read fibers 327. For instance, in the case depicted in FIG. 3E, the illuminating fibers 325 may expose the region of the wafer under the second transparent electrode 302, while the read fibers 327 may collect electroluminescence from the area of the LED structure 103 under the central transparent electrode 144. For example, as shown in FIG. 3F, the illumination channel 324 may include any number of illumination fibers 325 (e.g., 1, 2, 3, 4, 5, 6, 7, 8 and so on), while the read channel 326 may include any number of read fibers 327 (e.g., 1, 2, 3, 4, 5, 6, 7, 8 and so on).

It is noted herein that the configuration depicted in FIG. 3E is not limiting. For example, although not shown, the illumination and read channels may be reversed such that the illumination channel 324 illuminates the area of the LED structure 103 under the central electrode 144, while the read channel 326 collects electroluminescence from the area of the LED structure 103 under the second transparent electrode 302.

Figure 3G:
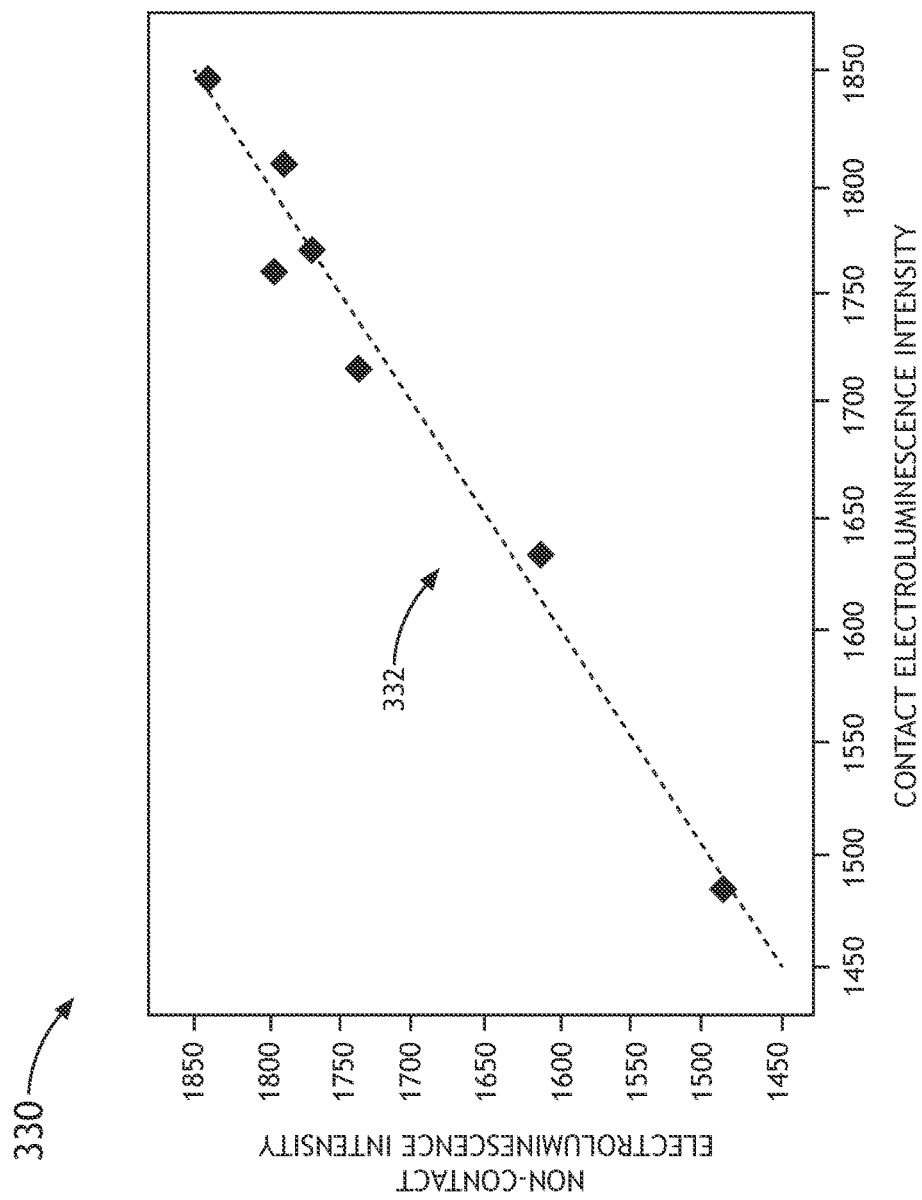
FIG. 3G illustrates a graph depicting the correlation between non-contact electroluminescence intensity and contact electroluminescence intensity, in accordance with one embodiment of the present disclosure.

FIG. 3G illustrates a graph 330 depicting the relationship between non-contact electroluminescence intensity and contact electroluminescence intensity. As shown in graph 330, there is a clear correspondence between the non-contact electroluminescence intensity and contact electroluminescence intensity measured under similar conditions, represented by data (and fit) 332.

Figure 4A:
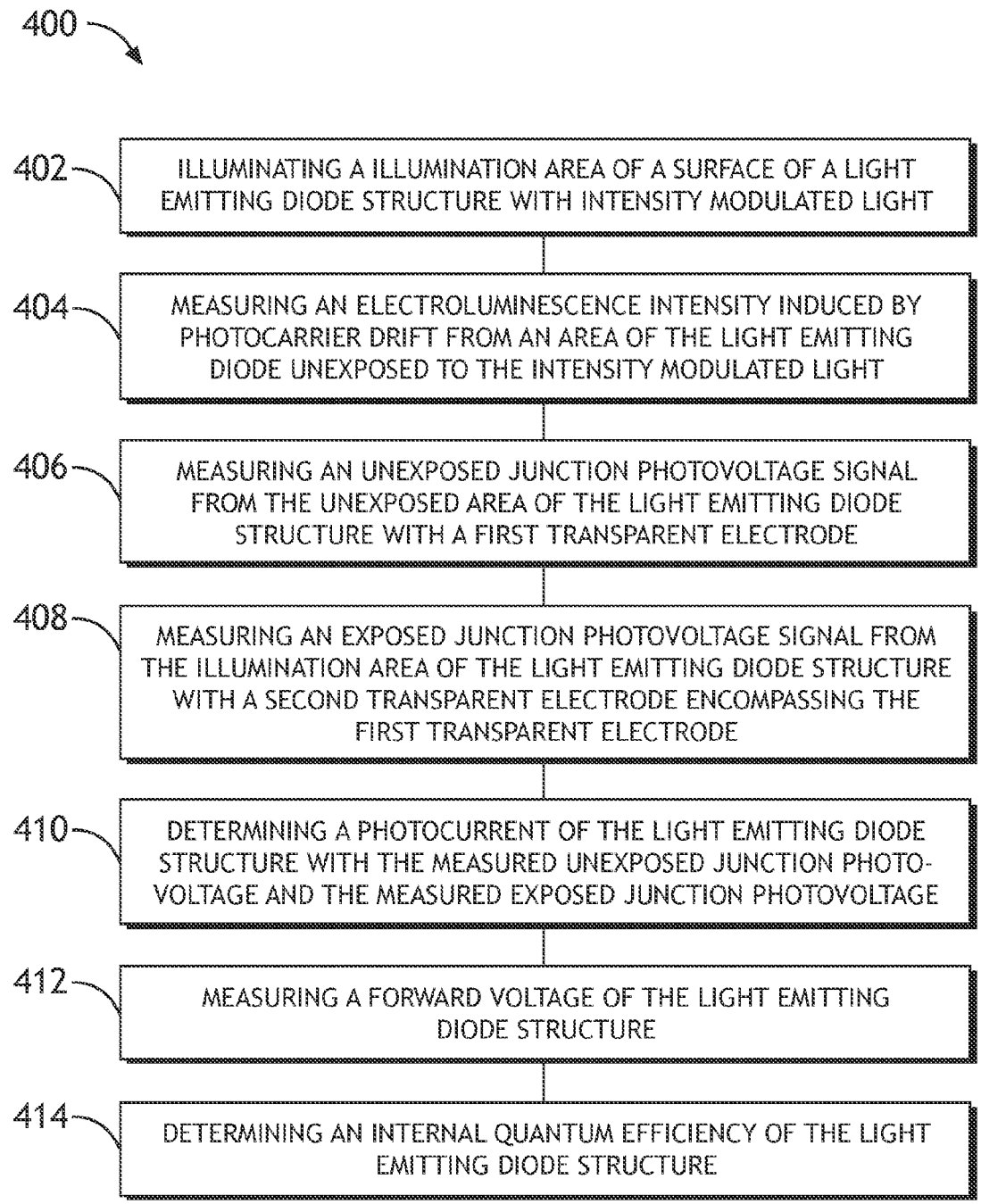
FIG. 4A is a flow diagram illustrating a method for contactless measurement of one or more characteristics of a LED structure, in accordance with one embodiment of the present disclosure.

FIG. 4A illustrates a flow diagram depicting a method 400 for contactless measurement of one or more characteristics of a LED structure, in accordance with one or more embodiments of the present disclosure. It is recognized herein that one or more of the steps of the method 400 may be implemented by one or more of the components and embodiments of system 100. It is noted, however, that method 400 is not limited to the structural limitations of system 100.

Step 402 illuminates an illumination area of a surface of a light emitting diode structure with intensity modulated light, as described previously herein.

Step 404 measures an electroluminescence intensity induced by photocarrier drift from an area of the light emitting diode structure 103 unexposed to the intensity modulated light with a luminescence sensor 122. For example, as shown in FIGS. 3A and 3B, the illumination source 110 and sensor 122 may be arranged such that there is a shadowed region 304 that is unexposed to the light 307. In this regard, the sensor 122 may be used to pick up any electroluminescence signal 126 that is stimulated by photocarrier drift (e.g., drift from area that is exposed (shown in FIG. 3B)).

Step 406 measures an unexposed junction photovoltage signal from the shadowed region 304 of the light emitting diode structure 103 with a first transparent electrode 144 positioned within the unexposed area and proximate to the surface of the light emitting diode structure 103. For example, as shown in FIG. 3A, the first transparent electrode 144 (e.g., central circular electrode) may measure junction photovoltage signal from the shadowed region 304 of the LED structure 103.

Step 408 measures an exposed junction photovoltage signal from the illumination area 307 of the light emitting diode structure 103 with a second transparent electrode 302 external to the first transparent electrode 144. For example, as shown in FIG. 3A, the second transparent electrode 302 (e.g., ring electrode surrounding central electrode) may measure junction photovoltage signal from the exposed area 307 of the LED structure 103. It is noted herein that both the first transparent electrode and the second transparent electrode may be disposed on the transparent element 143 (e.g., disposed on bottom portion of transparent element).

Step 410 determines a photocurrent density of the light emitting diode structure 103 with the measured unexposed junction photovoltage and the measured exposed junction photovoltage. For example, the controller 108 may calculate the photocurrent density of the light emitting diode structure 103 using with the measured unexposed junction photovoltage and the measured exposed junction photovoltage and equation (6) described above.

Step 412 measures a forward voltage of the light emitting diode structure. In one embodiment, the forward voltage $V_F$ is measured by (i) illuminating the surface of the light emitting diode structure with one or more light pulses, (ii) measuring a first junction photovoltage signal with the first transparent electrode 144; (iii) measuring a second junction photovoltage signal with the second transparent electrode 302; and (iii) determining the forward voltage $V_F$ of the light emitting diode structure 103 with the first junction photovoltage signal and the second junction photovoltage signal. The procedure for determining forward voltage $V_F$ in this context has been described previously herein.

Step 414 determines an internal quantum efficiency of the light emitting diode structure with the measured electroluminescence intensity from the unexposed area of the light emitting diode structure, the determined photocurrent density of the light emitting diode structure or the measured forward voltage of the diode structure. For example, the controller 108 may determine the IQE base on the measured and determined values the electroluminescence intensity, the photocurrent, and/or the measured forward voltage and equation (2) described previously herein.

Figure 4B:
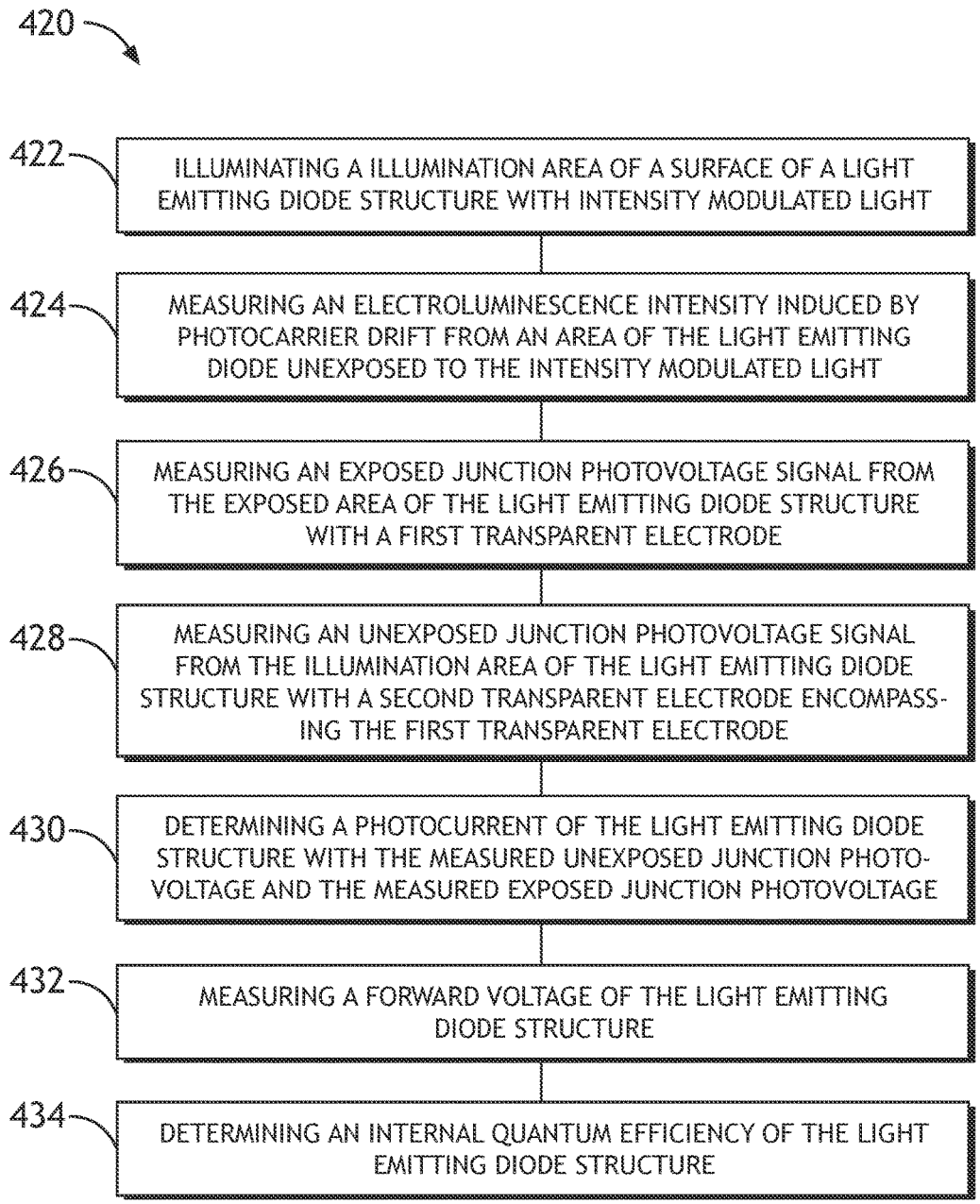
FIG. 4B is a flow diagram illustrating a method for contactless measurement of one or more characteristics of a LED structure, in accordance with one embodiment of the present disclosure.

FIG. 4B illustrates a flow diagram depicting a method 420 for contactless measurement of one or more characteristics of a LED structure, in accordance with one or more embodiments of the present disclosure. It is recognized herein that one or more of the steps of the method 420 may be implemented by one or more of the components and embodiments of system 100. It is noted, however, that method 400 is not limited to the structural limitations of system 100.

Step 422 illuminates an illumination area of a surface of a light emitting diode structure with intensity modulated light, as described previously herein.

Step 424 measures an electroluminescence intensity induced by photocarrier drift from an area of the light emitting diode unexposed to the intensity modulated light, as described previously herein.

Step 426 measures an exposed junction photovoltage signal from the exposed area of the light emitting diode structure with a first transparent electrode 144. For example, as shown in FIG. 3C, the first transparent electrode 144 (e.g., central circular electrode) may measure junction photovoltage signal from the exposed area 322 of the LED structure 103.

Step 428 measures an unexposed junction photovoltage signal from the illumination area of the light emitting diode structure with a second transparent electrode encompassing the first transparent electrode. For example, as shown in FIG. 3C, the second transparent electrode 302 (e.g., ring electrode surrounding central electrode) may measure a junction photovoltage signal from the unexposed area of the LED structure 103. It is again noted herein that both the first transparent electrode and the second transparent electrode may be disposed on the transparent element 143 (e.g., disposed on bottom portion of transparent element).

Step 430 determines a photocurrent density of the light emitting diode structure with the measured unexposed junction photovoltage and the measured exposed junction photovoltage, as described previously herein.

Step 432 measures a forward voltage of the light emitting diode structure, as described previously herein.

Step 434 determines internal quantum efficiency of the light emitting diode structure, as described previously herein.

Figure 4C:
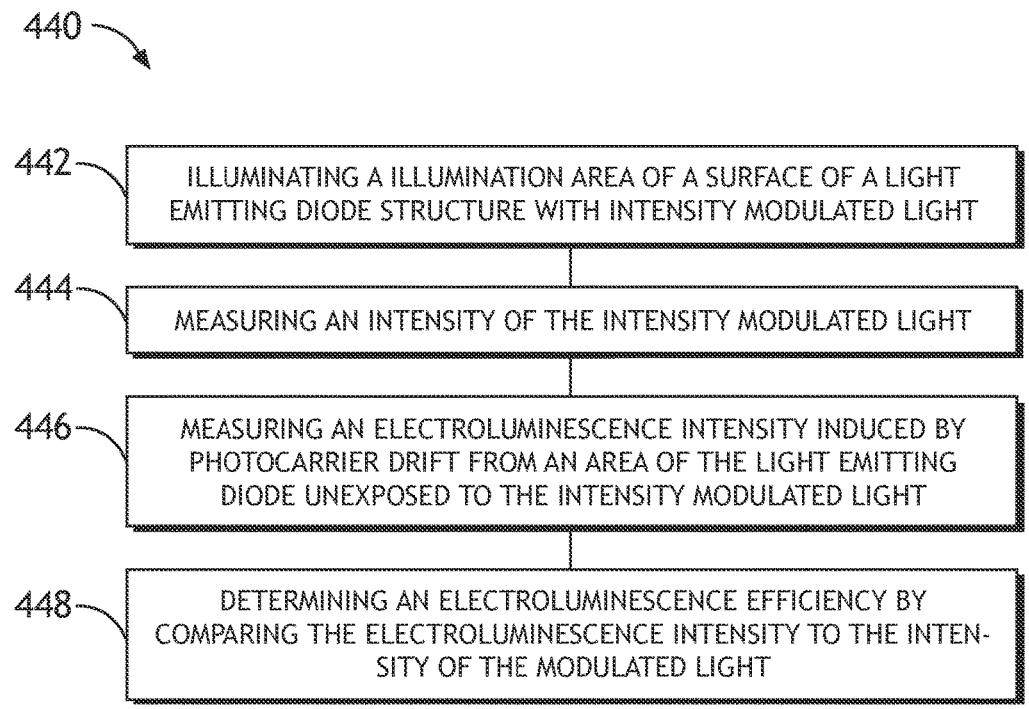
FIG. 4C is a flow diagram illustrating a method for contactless measurement of one or more characteristics of a LED structure, in accordance with one embodiment of the present disclosure.

FIG. 4C illustrates a flow diagram depicting a method 440 for contactless measurement of one or more characteristics of a LED structure, in accordance with one or more embodiments of the present disclosure. It is recognized herein that one or more of the steps of the method 440 may be implemented by one or more of the components and embodiments of system 100. It is noted, however, that method 400 is not limited to the structural limitations of system 100.

Step 442 illuminates a illumination area of a surface of a light emitting diode structure with intensity modulated light, as described previously herein. Step 444 measures an intensity of the intensity modulated light, as described previously herein. Step 446 measures an electroluminescence intensity induced by photocarrier drift from an area of the light emitting diode unexposed to the intensity modulated light, as described previously herein.

Step 448 determines an electroluminescence efficiency by comparing the electroluminescence intensity $I_{EL}$ to the intensity of the modulated light $I_{EX}$. For example, the controller 108 may determine the electroluminescence efficiency by comparing the intensity of the electroluminescence signal received from sensor 122 to the known or measured (from sensor 121) of the intensity of the modulated light from the illumination source 110. For instance, the controller 108 may compare the electroluminescence intensity $I_{EL}$ to the intensity of the modulated light $I_{EX}$ by calculating a ratio between $I_{EL}$ and $I_{EX}$ In another instance, the controller 108 may compare the electroluminescence intensity $I_{EL}$ to the intensity of the modulated light $I_{EX}$ by calculating a difference between $I_{EL}$ and $I_{EX}$.

It is further recognized that the controller 108 may execute one or more steps of any of the various methods described throughout the present disclosure. In this regard, the methods disclosed may be implemented as a set of program instructions. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented In one embodiment, the controller 108 includes one or more processors and memory (e.g., non-transitory memory). The one or more processors of controller 108 may include any one or more processing elements known in the art. In general, the term "processor" may be broadly defined to encompass any device having one or more processing elements, which execute program instructions from a non-transitory memory medium. The one or more processors may include any microprocessor-type device configured to execute software algorithms and/or program instructions. In one embodiment, the one or more processors may include any one of a desktop computer, mainframe computer system, workstation, image computer, parallel processor, or other computer system (e.g., networked computer) configured to execute a set of program instructions configured to operate the system 100, as described throughout the present disclosure. It should be recognized that the steps described throughout the present disclosure may be carried out by a single controller or, alternatively, multiple controllers. The memory may include any storage medium known in the art suitable for storing program instructions executable by the associated one or more processors of controller 108. For example, the memory may include, but is not limited to, a read-only memory, a random access memory, a magnetic or optical memory device (e.g., disk), a magnetic tape, a solid state drive and the like. In another embodiment, it is noted herein that the memory is configured to store one or more results from the one or more of the various sub-systems of system 100. In another embodiment, the memory may be located remotely with respect to the physical location of the processors and controller 108. For instance, the one or more processors of controller 108 may access a remote memory (e.g., server), accessible through a network (e.g., internet, intranet and the like).

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. An apparatus for contactless measurement of one or more characteristics of a light emitting diode structure comprising:
   an illumination unit including an illumination source for illuminating an illumination area of a substrate including a light emitting diode structure with light of a selected intensity amplitude, the light including at least one of intensity modulated light or pulsed light, the light suitable for stimulating photoluminescence within at least a first area of the light emitting diode structure of the illumination area;
   a luminescence measurement unit including at least one optical sensor configured to measure a luminescence signal from the first area of the LED structure within the illumination area;
   a junction photovoltage measurement unit including at least a first transparent electrode positioned proximate to the light emitting diode structure and configured to transmit light from the illumination source to the first area of the LED structure, wherein the first transparent electrode is configured to measure a junction photovoltage signal of the light emitting diode structure corresponding with the first area within the illuminated area, wherein the area of the first electrode is smaller than the illumination area illuminated by the illumination unit; and a controller communicatively coupled to at least the luminescence measurement unit, the junction photovoltage measurement unit and the illumination unit, the controller configured to:

control one or more characteristics of the light from the illumination source;

receive one or more measurements of the luminescence signal from the luminescence measurement unit;

receive one or more measurements of the junction photovoltage signal from the junction photovoltage measurement unit; and determine at least one of an internal quantum efficiency or an internal injection efficiency of the light emitting diode structure based on one or more characteristics of the received one or more measurements of the luminescence signal and one or more characteristics of the received one or more measurements of the junction photovoltage signal.

2. The apparatus of claim 1, wherein the controller is further configured to:

determine at least one of an internal quantum efficiency or an internal injection efficiency of the light emitting diode structure with at least one of a determined junction photovoltage forward voltage of the light emitting diode structure from the luminescence area, a photocurrent density of the light emitting diode structure or an intensity of the electroluminescence component of the luminescence signal.

3. The apparatus of claim 1, wherein the illumination source comprises:

an illumination source configured to emit light modulated at a selected modulation frequency.

4. The apparatus of claim 1, wherein the illumination source comprises:

an illumination source configured to emit pulsed light of a selected magnitude and pulse duration.

5. The apparatus of claim 1, wherein the illumination source comprises:

at least one of a light emitting diode, a laser or a filtered flash lamp.

6. The apparatus of claim 1, wherein the junction photovoltage measurement unit further includes:

one or more signal processing elements.

7. The apparatus of claim 6, wherein the one or more signal processing elements comprise:

at least one of a preamplifier or detector.

8. The apparatus of claim 1, wherein the luminescence measurement unit further includes:

one or more signal processing elements.

9. The apparatus of claim 8, wherein the one or more signal processing elements comprise:

at least one of a preamplifier or detector.

10. The apparatus of claim 1, wherein the substrate including a light emitting diode structure is disposed on a chuck.

11. The apparatus of claim 10, further comprising:

a signal generator electrically coupled to the chuck via a switch.

12. The apparatus of claim 1, wherein the one or more characteristics of the luminescence signal comprise:

at least one of a transient of the luminescence signal or an amplitude of the luminescence signal.

13. The apparatus of claim 1, wherein the one or more characteristics of the junction photovoltage signal comprise:

at least one of a transient of the junction photovoltage signal or an amplitude of the junction photovoltage signal.

14. The apparatus of claim 1, further comprising:

a transparent element configured to secure at least the first transparent electrode.

15. The apparatus of claim 1, further comprising:

at least one conducting pad electrically coupling a p-layer of the light emitting diode structure to an n-layer of the light emitting diode structure.

16. The apparatus of claim 1, further comprising:

an additional electrode disposed on a vertical stage and positioned proximate to the light emitting diode structure.

17. A method for contactless measurement of one or more characteristics of a light emitting diode structure comprising:

illuminating an illumination area of a surface of a light emitting diode structure with one or more light pulses;

measuring a transient of a luminescence signal from a luminescence area within the illumination area with a luminescence sensor;

measuring a transient of a junction photovoltage signal from the luminescence area within the illumination area with a transparent electrode positioned within the illumination area and proximate to the surface of the light emitting diode structure;

determining a junction photovoltage forward voltage of the light emitting diode structure from the luminescence area;

determining a photocurrent density of the light emitting diode structure;

determining an intensity of an electroluminescence component of the luminescence signal; and determining at least one of an internal quantum efficiency or an internal injection efficiency of the light emitting diode structure with at least one of the determined junction photovoltage forward voltage of the light emitting diode structure from the luminescence area, the photocurrent density of the light emitting diode structure or the intensity of the electroluminescence component of the luminescence signal.

18. The method of claim 17, wherein the junction photovoltage forward voltage of the luminescence area is determined based on the amplitude of the junction photovoltage signal measured from the luminescence area with the transparent electrode.

19. The method of claim 17, wherein the determining a photocurrent density of the LED structure comprises:

determining a derivative of the transient of the JPV signal at a front edge of the JPV signal;

acquiring a capacitance of a p-n junction of the LED structure; and calculating the photocurrent density of the LED structure with the derivative of the transient of the JPV signal at a front edge of the JPV signal and the capacitance of the p-n junction of the LED structure.

20. The method of claim 17, wherein the determining an intensity of an electroluminescence component of the luminescence signal comprises:

applying pulsed illumination to the light emitting diode structure having a first time interval corresponding with the junction photovoltage forward voltage being lower than a turn on voltage of the electroluminescence signal based on the transient of the junction photovoltage;

applying pulsed illumination to the light emitting diode structure having a second time interval corresponding with the junction photovoltage forward voltage being higher than the turn on voltage of the electroluminescence signal based on the transient of the junction photovoltage; and determining the intensity of the electroluminescence component of the luminescence signal by calculating a difference between a first luminescence signal acquired during the second time interval and a second luminescence signal acquired during the first time interval.

21. The method of claim 17, wherein the determining an intensity of an electroluminescence component of the luminescence signal comprises:
upon terminating the illumination of the light emitting diode structure, identifying a value of the luminescence signal following a selected time of decay of the luminescence signal.

22. The method of claim 17, wherein the determining an intensity of an electroluminescence component of the luminescence signal comprises:
establishing a duration time of the one or more light pulses so as to illuminate the illumination area with a first one or more light pulses having a first duration sufficient to establish a steady-state condition when forward voltage is higher than electroluminescence turn-on voltage;
establishing a duration time of the one or more light pulses so as to illuminate the illumination area with a second one or more light pulses having a second duration shorter than the first duration and sufficient to establish a non-steady state condition when the forward voltage is lower than electroluminescence turn-on voltage; and
determining the intensity of the electroluminescence signal component by calculating the difference between a first luminescence intensity acquired during illumination with the first one or more light pulses and a second luminescence intensity acquired during illumination with the second one or more light pulses.

23. A method for contactless measurement of one or more characteristics of a light emitting diode structure comprising:
illuminating an illumination area of a surface of a light emitting diode structure with one or more light pulses;
measuring a transient of a luminescence signal from a luminescence area within the illumination area of the light emitting diode structure with a luminescence sensor;
determining a first luminescence intensity at a first time of the measured transient of the luminescence signal from the light emitting diode structure;
determining a second luminescence intensity at a second time different from the first time of the measured transient of the luminescence signal from the light emitting diode structure; and
determining an intensity of the electroluminescence component of the luminescence signal from the light emitting diode structure with the first luminescence intensity and the second luminescence intensity.

24. The method of claim 23, further comprising:
illuminating an illumination area of a surface of a calibration wafer having a known internal quantum efficiency with one or more light pulses;
measuring a transient of a luminescence signal from a luminescence area within the illumination area of the calibration wafer with a luminescence sensor;
determining a first luminescence intensity at a first time of the measured transient of the luminescence signal from the calibration wafer;
determining a second luminescence intensity at a second time different from the first time of the measured transient of the luminescence signal from the calibration wafer;
determining an intensity of the electroluminescence component of the luminescence signal from the calibration wafer based on the first luminescence intensity and the second luminescence intensity; and
determining an internal quantum efficiency of the light emitting diode structure with the intensity of electroluminescence component from the light emitting diode structure, the intensity of the electroluminescence component from the calibration wafer and the known internal quantum efficiency of the calibration wafer.

25. A method for contactless measurement of one or more characteristics of a light emitting diode structure comprising:
illuminating an illumination area of a surface of a light emitting diode structure with one or more first light pulses of a first pulse duration;
illuminating the illumination area of the surface of the light emitting diode structure with one or more second light pulses of a second pulse duration;
measuring a first luminescence intensity from the light emitting diode structure stimulated by the one or more first light pulses;
measuring a second luminescence intensity from the light emitting diode structure stimulated by the one or more second light pulses; and
determining an intensity of the electroluminescence component of the luminescence signal from the light emitting diode structure based on the first luminescence intensity and the second luminescence intensity.

26. The method of claim 25, further comprising:
illuminating an illumination area of a surface of a calibration wafer with a known internal quantum efficiency with one or more first light pulses of a first pulse duration;
illuminating the illumination area of the surface of the calibration wafer with one or more second light pulses of a second pulse duration;
measuring a first luminescence intensity from the calibration wafer stimulated by the one or more first light pulses;
measuring a second luminescence intensity from the calibration wafer stimulated by the one or more second light pulses;
determining an intensity of the electroluminescence component of the luminescence signal from the calibration wafer based on the first luminescence intensity and the second luminescence intensity; and
determining an internal quantum efficiency of the light emitting diode structure with the intensity of electroluminescence component from the light emitting diode structure, the intensity of the electroluminescence component from the calibration wafer and the known internal quantum efficiency of the calibration wafer.

27. A method for contactless measurement of one or more characteristics of a light emitting diode structure comprising:
illuminating a illumination area of a surface of a light emitting diode structure with intensity modulated light;

measuring an electroluminescence intensity induced by photocarrier drift from an area of the light emitting diode unexposed to the intensity modulated light with a luminescence sensor;

measuring an unexposed junction photovoltage signal from the unexposed area of the light emitting diode structure with a first transparent electrode positioned within the unexposed area and proximate to the surface of the light emitting diode structure;

measuring an exposed junction photovoltage signal from the illumination area of the light emitting diode structure with a second transparent electrode external to the first transparent electrode, positioned within the illumination area and proximate to the surface of the light emitting diode structure;

determining a photocurrent density of the light emitting diode structure with the measured unexposed junction photovoltage and the measured exposed junction photovoltage;

measuring a forward voltage of the light emitting diode structure; and determining an internal quantum efficiency of the light emitting diode structure with at least one of the measured electroluminescence intensity from the unexposed area of the light emitting diode structure, the determined photocurrent density of the light emitting diode structure or the measured forward voltage of the diode structure.

28. The method of claim 27, wherein the measuring a forward voltage of the light emitting diode structure comprises:

illuminating the surface of the light emitting diode structure with one or more light pulses;

measuring a first junction photovoltage signal with the first transparent electrode;

measuring a second junction photovoltage signal with the second transparent electrode; and determining the forward voltage of the light emitting diode structure with the first junction photovoltage signal and the second junction photovoltage signal.

29. A method for contactless measurement of one or more characteristics of a light emitting diode structure comprising:

illuminating an illumination area of a surface of a light emitting diode structure with intensity modulated light;

measuring an electroluminescence intensity induced by photocarrier drift from an area of the light emitting diode unexposed to the intensity modulated light with a luminescence sensor;

measuring an exposed junction photovoltage signal from the exposed area of the light emitting diode structure with a first transparent electrode positioned within the exposed area and proximate to the surface of the light emitting diode structure;

measuring an unexposed junction photovoltage signal from the illumination area of the light emitting diode structure with a second transparent electrode encompassing the first transparent electrode and proximate to the surface of the light emitting diode structure;

determining a photocurrent density of the light emitting diode structure with the measured unexposed junction photovoltage and the measured exposed junction photovoltage;

measuring a forward voltage of the light emitting diode structure; and determining an internal quantum efficiency of the light emitting diode structure with at least one of the measured electroluminescence intensity from the unexposed area of the light emitting diode structure, the determined photocurrent density of the light emitting diode structure or the measured forward voltage of the diode structure.

30. A method for contactless measurement of one or more characteristics of a light emitting diode structure comprising:

illuminating a illumination area of a surface of a light emitting diode structure with intensity modulated light;

measuring an intensity of the intensity modulated light;

measuring an electroluminescence intensity induced by photocarrier drift from an area of the light emitting diode structure unexposed to the intensity modulated light with a luminescence sensor; and determining an electroluminescence efficiency by comparing the electroluminescence intensity to the intensity of the modulated light.

* * * * *